(12) United States Patent
Underwood et al.

(10) Patent No.: US 7,759,103 B2
(45) Date of Patent: Jul. 20, 2010

(54) EXTRACELLULAR SERINE PROTEASE

(75) Inventors: Lowell J. Underwood, Little Rock, AR (US); Timothy J. O'Brien, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 11/251,455

(22) Filed: Oct. 14, 2005

(65) Prior Publication Data
US 2006/0068483 A1 Mar. 30, 2006

Related U.S. Application Data

(60) Division of application No. 09/137,944, filed on Aug. 21, 1998, now Pat. No. 7,067,250, which is a continuation-in-part of application No. 08/915,659, filed on Aug. 21, 1997, now Pat. No. 7,014,993.

(51) Int. Cl.
*C12N 9/48* (2006.01)
*C12N 9/00* (2006.01)

(52) U.S. Cl. ...................... 435/212; 435/183

(58) Field of Classification Search ............ None
See application file for complete search history.

(56) References Cited

OTHER PUBLICATIONS

Yoshida et al. (1998) Gene, vol. 213, p. 9-16.*
Scanlan et al. (1994) Proc. Natl. Acad. Sci. USA, vol. 91, p. 5657-5661.*
Underwood et al. (1999) Cloning of Tumor-associated Differentially Expressed Gene-14, a Novel Serine Protease Overexpressed by Ovarian Carcinoma, Cancer Research, vol. 59, p. 4435-4439.*
Hill et al. (1998) Biochem. Biophys. Res. Comm. 244:573-577.*
Guo et al. (2004) Proc. Natl. Acad. Sci. USA 101: 9205-9210.*
Lazar et al. (1988) Mol. Cell. Biol. 8:1247-1252.*
Mattila et al., 1994, Electrophoresis, vol. 15, pp. 721-725.*
Shimizu-Okabe et al., 2001, Molecular Neuroscience, vol. 12, pp. 2747-2751.*
Mitsui et al., 1999, Eur. J. Biochem, vol. 260, p. 627-634.*

* cited by examiner

*Primary Examiner*—Richard Hutson
*Assistant Examiner*—Alexander D Kim
(74) *Attorney, Agent, or Firm*—Benjamin Aaron Adler

(57) ABSTRACT

The present invention provides a DNA encoding a human Tumor Antigen Derived Gene-14 (TADG-14) protein selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein. Also, provided is a vector capable of expressing the DNA of the present invention adapted for expression in a recombinant cell and regulatory elements necessary for expression of the DNA in the cell.

1 Claim, 16 Drawing Sheets

1) Normal Ovary  2) Tumor
3) Normal Ovary  4) Tumor

1) Normal Ovary  2) Tumor
3) Normal Ovary  4) Tumor

```
201       PRIMER
Prom    WVLTAAHC KK   PNLQV.....F   LGKHNLRQRE   SSQEQSSVVR   250  AVIHPDY...
Tadg14  WVVTAAHC KK   PKYTV.....R   LGDHSLQNKD                GPEQEIPVVQ   SIPHPCY...
Try1    WVVSAGHC YK   SRIQV.....R   LGEHNIEVLE   GNEQFINAAK   IIRHPQY...
Scce    WVLTAAHC KM   NEYTV.....H   LGSDTLGDRR   A..QRIKASK   SFRHPGY...
Heps    WVLTAAHC FP   ERNRVLSRWR    VFAGAVAQAS   PHGLGLGVQA   VVYHGGYLFF 251                                                           300
Prom    ...DAAASHDQ   DIMLL RLARP   AKLSELIQPL   PLERDCSA...  NTTSCHILGW
Tadg14  NSSDVEDHNH    DLMLL QLRDQ   ASLGSKVKPI   SLADHCTQ...  PGQNCTVSGW
Try1    ...DRKTLNN    DIMLI KLSSR   AVINARVSTI   SLPTAPPA...  TGTKCLISGW
Scce    ST...QTHVN    DLMLV KLNSQ   ARLSSMVKKV   RLPSRCEP...  PGTTCTVSGW
Heps    RDPNSEENSN    DIALV HLSSP   LPLTEYIQPV   CLPAAGQALV   DGKICTVTGW 301                                                           350
Prom    GKTAD..GDF    PDTIQCAYIH    LVSREECEHA   ..TPGQITQN   MLCAGDEKYG
Tadg14  GTVTSPRENF    PDTLNCAEVK    IFPQKKCEDA   ..YPGQITDG   MVCAGSSK.G
Try1    GNTASSGADY    PDELQCLDAP    VLSQAKCEAS   ..YPGKITSN   MFCVGFLEGG
Scce    GTTTSPDVTF    PSDLMCVDVK    LISPQDCTKV   ..YKDLLENS   MLCAGIPDSK
Heps    GNTQYYGQQ.    AGVLQEARVP    IISNDVCNGA   DFYGNQIKPK   MFCAGYPEGG 351
Prom    KDSCQ GDSGG   SEQ ID No. 1
Tadg14  ADTCQ GDSGG   SEQ ID No. 2
Try1    KDSCQ GDSGG   SEQ ID No. 3
Scce    KNACN GDSGG   SEQ ID No. 4
Heps    IDACQ GDSGG   SEQ ID No. 5
              PRIMER
```

Fig. 2

```
   1 CTGTAGCAGGCAGAGCTTACCAAGTCTCTCCGAACTCAAATGGAAGAAATACCTTATGAA   60
  61 TGTAAGAATGTAGGGGGTCATGGCTTGTAATTTACACAGTGTAAATGAAACCATCCTAGA  120
 121 GGATTATGAGGAATCCTTTCTATGTGATTTTCAATCATAGCAAGCAAGAAAGGCTCCAGT  180
 181 GTCAAGGTAGTTCAGCTCTTACAGGATATAAAACAGTCCATACTTGAGAGAAAAAACTTA  240
 241 GATCTGAGTGATGGAATGTGAAGCAAATCTTTCAAAATCAGTAGACATTTCTTGGACATA  300
 301 AAACACAGATGAGGAAAGGGCTTCAAATTAGAAGTTACGTAATCACCATCAGAAAGTTCA  360
 361 TGTTTGGTAAATTCTGTTACTAGAAATGTAGGAAATTCAGGTATAGCTTTGAATCCCAAT  420
 421 TACACATTGGTCAGTGGGAAAACTAAGGGCCTCCAACAGGCAAATTCAGGGAGGATAGGT  480
 481 TTCAGGGAATGCCCTGGATTCTGGAAGACCTCACCATGGACGCCCCGACCTCGTGCGG   540
                                    M   G   R   P   R   P   A   A  -
 541 CCAAGACGTGGATGTTCCTGCTCTTGCTGGGGGGAGCCTGGGCAGGACACTCCAGGGCAC  600
      K   T   W   M   F   L   L   L   G   G   A   W   A   G   H   S   R   A   Q  -
 601 AGGAGGACAAGGTGCTGGGGGGTCATGAGTGCCAACCCCATTCGCAGCCTTGGCAGGCGG  660
      E   D   K   V   L   G   G   H   E   C   Q   P   H   S   Q   P   W   Q   A   A  -
 661 CCTTGTTCCAGGGCCAGCAACTACTCTGTGGCGGTGTCCTTGTAGGTGGCAACTGGGTCC  720
      L   F   Q   G   Q   Q   L   L   C   G   G   V   L   V   G   N   W   V   L  -
 721 TTACAGCTGCCCACTGTAAAAAACCGAAATACACAGTACGCCTGGGAGACCACAGCCTAC  780
      T   A   A   H+  C   K   K   P   K   Y   T   V   R   L   G   D   H   S   L   Q  -
 781 AGAATAAAGATGGCCCAGAGCAAGAAATACCTGTGGTTCAGTCCATCCCACACCCCTGCT  840
      N   K   D   G   P   E   Q   E   I   P   V   V   Q   S   I   P   H   P   C   Y  -
 841 ACAACAGCAGCGATGTGGAGGACCACAACCATGATCTGATGCTTCTTCAACTGCGTGACC  900
      N   S   S   D   V   E   D   H   N   H   D+  L   M   L   L   Q   L   R   D   Q  -
 901 AGGCATCCCTGGGGTCCAAAGTGAAGCCCATCAGCCTGGCAGATCATTGCACCCAGCCTG  960
      A   S   L   G   S   K   V   K   P   I   S   L   A   D   H   C   T   Q   P   G  -
 961 GCCAGAAGTGCACCGTCTCAGGCTGGGGCACTGTCACCAGTCCCCGAGAGAATTTTCCTG 1020
      Q   K   C   T   V   S   G   W   G   T   V   T   S   P   R   E   N   F   P   D  -
1021 ACACTCTCAACTGTGCAGAAGTAAAAATCTTTCCCCAGAAGAAGTGTGAGGATGCTTACC 1080
      T   L   N   C   A   E   V   K   I   F   P   Q   K   K   C   E   D   A   Y   P  -
1081 CGGGGCAGATCACAGATGGCATGGTCTGTGCAGGCAGCAGCAAAGGGGCTGACACGTGCC 1140
      G   Q   I   T   D   G   M   V   C   A   G   S   S   K   G   A  (D)  T   C   Q  -
1141 AGGGCGATTCTGGAGGCCCCCTGGTGTGTGATGGTGCACTCCAGGGCATCACATCCTGGG 1200
      G   D  (S+) G   G   P   L   V   C   D   G   A   L   Q   G   I   T   S   W  (G) -
1201 GCTCAGACCCCTGTGGGAGGTCCGACAAACCTGGCGTCTATACCAACATCTGCCGCTACC 1260
      S   D   P   C   G   R   S   D   K   P  (G)  V   Y   T   N   I   C   R   Y   L  -
1261 TGGACTGGATCAAGAAGATCATAGGCAGCAAGGGCTGATTCTAGGATAAGCACTAGATCT 1320
      D   W   I   K   K   I   I   G   S   K   *    SEQ ID No. 6
1321 CCCTTAATAAACTCACGGAATTC  SEQ ID No. 7
```

└──┘ = Kozak's Consensus sequence

+ = Conserved amino acids of catalytic triad H, D, S

[NSS] = Possible N - linked glycosylation site

⌣ = Poly - adenylation signal

▢ = Conserved nt of catalytic triad

◯ = aa required for formation of an oxyanion hole for catalytic activity

[FLLL] = Secretion signal sequence

Fig. 6

```
Neur  477 AGAGGCCACCATGGGACGCCCCCACCCTGTGCAATCCAGCCGTGGATCC 526
          |||  ||||||||||||||||||| |||  ||||  |  ||  ||||||||
T14   506 AGACCTCACCATGGGACGCCCCGACCTCGTGCGGCCAAGACGTGGATGT 555

527 TTCTGCTTCTGTTCATGGGAGCGTGGGCAGGGCTCACCAGAGCTCAGGGC 576
          | |||||  || |   |||||| ||||||||| | ||||  || ||||
      556 TCCTGCTCTTGCTGGGGGGAGCCTGGGCAGGACACTCCAGGGCACAGGAG 605

577 TCCAAGATCCTGGAAGGTCGAGAGTGTATACCCCACTCCCAGCCTTGGCA 626
          ||||  | ||||  |||| |||||  || ||||||||||||||||||
      606 GACAAGGTGCTGGGGGGTCATGAGTGCCAACCCCATTCGCAGCCTTGGCA 655

627 GGCAGCCTTGTTCCAGGGCGAGAGACTGATCTGTGGGGGTGTCCTGGTTG 676
          ||| |||||||||||||||  ||  ||||||| |||||||| ||  |
      656 GGCGGCCTTGTTCCAGGGCCAGCAACTACTCTGTGGCGGTGTCCTTGTAG 705

677 GAGACAGATGGGTCCTCACGGCAGCCCACTGCAAAAAACAGAAGTACTCC 726
          | ||  |||||||| || || |||||||||| |||||| |||  |||  |
      706 GTGGCAACTGGGTCCTTACAGCTGCCCACTGTAAAAAACCGAAATACACA 755

727 GTGCGTCTGGGTGATCATAGCCTCCAGAGCAGAGATCAGCCGGAGCAGGA 776
          || || |||||| || || |||||  |||  || ||||| || |||||
      756 GTACGCCTGGGAGACCACAGCCTACAGAATAAAGATGGCCCAGAGCAAGA 805

777 GATCCAGGTGGCTCAGTCTATCCAGCATCCTTGCTACAACAACAGCAACC 826
          || |  |||| ||||||| ||||  || || ||||||||||| ||||  |
      806 AATACCTGTGGTTCAGTCCATCCCACACCCCTGCTACAACAGCAGCGATG 855

827 CAGAAGATCACAGTCACGATATAATGCTCATTCGACTGCAGAACTCAGCA 876
          || || |||| || |||  | ||||| ||| |||||  ||  ||
      856 TGGAGGACCACAACCATGATCTGATGCTTCTTCAACTGCGTGACCAGGCA 905

877 AACCTCGGGGACAAGGTGAAGCCGGTCCAACTGGCCAATCTGTGTCCCAA 926
          |||  ||| |||  ||||||| |  ||||| |  |||||  || ||  |
      906 TCCCTGGGGTCCAAAGTGAAGCCCATCAGCCTGGCAGATCATTGCACCCA 955

927 AGTTGGCCAGAAGTGCATCATATCAGGCTGGGGCACTGTCACCAGCCCTC 976
          |||||||||||||||| |  | ||||||||||||||||||||| ||  |
      956 GCCTGGCCAGAAGTGCACCGTCTCAGGCTGGGGCACTGTCACCAGTCCCC 1005

977 AAGAGAACTTTCCAAACACCCTCAACTGTGCGGAAGTGAAAATCTATTCC 1026
          ||||||  |||||  ||| |||||||||||| |||| ||||| ||| |  ||
     1006 GAGAGAATTTTCCTGACACTCTCAACTGTGCAGAAGTAAAAATCTTTCCC 1055
```

Fig. 7A

```
1027 CAGAACAAGTGTGAGAGAGCCTATCCAGGGAAGATCACCGAGGGCATGGT 1076
     ||||| |||||||||   || || || ||| |||||||| || ||||||||
1056 CAGAAGAAGTGTGAGGATGCTTACCCGGGGCAGATCACAGATGGCATGGT 1105

1077 CTGTGCTGGCAGCAGCAATGGAGCTGACACGTGCCAGGGTGACTCAGGAG 1126
     |||||| |||||||||||| || |||||||||||||||| || || ||||
1106 CTGTGCAGGCAGCAGCAAAGGGGCTGACACGTGCCAGGCGATTCTGGAG 1155

1127 GCCCTCTGGTGTGCGACGGGATGCTCCAGGGCATCACCTCATGGGGCTCA 1176
     |||| |||||||| || ||     |||||||||||| || |||||||||
1156 GCCCCTGGTGTGTGATGGTGCACTCCAGGGCATCACATCCTGGGGCTCA 1205

1177 GACCCCTGTGGGAAACCCGAGAAACCTGGAGTCTACACCAAAATCTGCCG 1226
     |||||||||||||   ||||  |||||||||| ||||| ||||  |||||||
1206 GACCCCTGTGGGAGGTCCGACAAACCTGGCGTCTATACCAACATCTGCCG 1255

1227 CTACACTACCTGGATCAAGAAGACCATGGACAACAGGGACTGATCCTGG 1275
     ||||    |||||||||||||||  ||| | || || || ||||| || |
1256 CTACCTGGACTGGATCAAGAAGATCATAGGCAGCAAGGGCTGATTCTAG 1304
```

Neur        SEQ ID No. 8

T14         SEQ ID No. 9

Fig. 7B

```
Tadg14   1 MGRPRPRAAKTWMFLLLLGGAWAGHSRAQEDKVLGGHECQPHSQPWQAAL  50
           ||||  |  | · | ·   |||   |||||  · |||    | : |    ||  ||||||||||||
Neurop   1 MGRPPPCAIQPWILLLLFMGAWAGLTRAQGSKILEGRECIPHSQPWQAAL  50

51 FQGQQLLCGGVLVGGNWVLTAAHCKKPKYTVRLGDHSLQNKDGPEQEIPV 100
           |||:·|:||||||| ||||||||||  ||·||||||||||·:| |||||  |
        51 FQGERLICGGVLVGDRWVLTAAHCKKQKYSVRLGDHSLQSRDQPEQEIQV 100

101 VQSIPHPCYNSSDVEDHNHDLMLLQLRDQASLGSKVKPISLADHCTQPGQ 150
           |||  ||||| · | ·  ||| · || : || : · | ··    | · ||    ||||:    || · |    · ||
       101 AQSIQHPCYNNSNPEDHSHDIMLIRLQNSANLGDKVKPVQLANLCPKVGQ 150

151 KCTVSGWGTVTSPRENFPDTLNCAEVKIFPQKKCEDAYPGQITDGMVCAG 200
           || :|||||||||·||||·||||||||||: | ||| ||||·||:||||||
       151 KCIISGWGTVTSPQENFPNTLNCAEVKIYSQNKCERAYPGKITEGMVCAG 200

201 SSKGADTCQGDSGGPLVCDGALQGITSWGSDPCGRSDKPGVYTNICRYLD 250
           || ||||||||||||||||||| ||||||||||||: :|||||| ||||
       201 SSNGADTCQGDSGGPLVCDGMLQGITSWGSDPCGKPEKPGVYTKICRYTT 250

251 WIKKIIGSKG 260   SEQ ID No. 7
           ||||  · ·:
       251 WIKKTMDNRD 260   SEQ ID No. 10
```

Fig. 8

```
   1 CTGTAGCAGGCAGAGCTTACCAAGTCTCTCCGAACTCAAATGGAAGAAATACCTTATGAA
  61 TGTAAGAATGTAGGGGGTCATGGCTTGTAATTTACACAGTGTAAATGAAACCATCCTAGA
 121 GGATTATGAGGAATCCTTTCTATGTGATTTTCAATCATAGCAAGCAAGAAAGGCTCCAGT
 181 GTCAAGGTAGTTCAGCTCTTACAGGATATAAAACAGTCCATACTTGAGAGAAAAAACTTA
 241 GATCTGAGTGATGGAATGTGAAGCAAATCTTTCAAAATCAGTAGACATTTCTTGGACATA
 301 AAACACAGATGAGGAAAGGGCTTCAAATTAGAAGTTACGTAATCACCATCAGAAAGTTCA
 361 TGTTTGGTAAATTCTGTTACTAGAAATGTAGGAAATTCAGGTATAGCTTTGAATCCCAAT
 421 TACACATTGGTCAGTGGGAAAACTAAGGGCCTCCAACAGGCAAATTCAGGGAGGATAGGT
 481 TTCAGGGAATGCCCTGGATTCTGGAAGACCTCACCATGGACGCCCCCGACCTCGTGCGG
                                        M   G   R   P   R   A   A
 541 CCAAGACGTGGATGTTCCTGCTCTTGCTGGGGGGAGCCTGGGCAGGACACTCCAGGGCAC
      S   T   W   M   F   L   L   L   L   G   G   A   W   A   G   H   S   R   A   Q
 601 AGGAGGACAAGGTGCTGGGGGGTCATGAGTGCCAACCCCATTCGCAGCCTTGGCAGGCGG
      E   D   K   V   L   G   G   H   E   C   Q   P   H   S   Q   P   W   Q   A   A
 661 CCTTGTTCCAGGGCCAGCAACTACTCTGTGGCGGTGTCCTTGTAGGTGGCAACTGGGTCC
      L   F   Q   G   Q   Q   L   L   C   G   G   V   L   V   G   N   W   V   L
 721 TTACAGCTGCCCACTGTAAAAAACCGAAATACACAGTACGCCTGGGAGACCACAGCCTAC
      T   A   A   H   C   K   K   P   K   Y   T   V   R   L   G   D   H   S   L   Q
 781 AGAATAAAGATGGCCCAGAGCAAGAAATACCTGTGGTTCAGTCCATCCCACACCCCTGCT
      N   K   D   G   P   E   Q   E   I   P   V   V   Q   S   I   P   H   P   C   Y
 841 ACAACAGCAGCGATGTGGAGGACCACAACCATGATCTGATGCTTCTTCAACTGCGTGACC
      N   S   S   D   V   E   D   H   N   H   D   L   M   L   L   Q   L   R   D   Q
 901 AGGCATCCCTGGGGTCCAAAGTGAAGCCCATCAGCCTGGCAGATCATTGCACCCAGCCTG
      A   S   L   G   S   K   V   K   P   I   S   L   A   D   H   C   T   Q   P   G
 961 GCCAGAAGTGCACCGTCTCAGGCTGGGGCACTGTCACCAGTCCCCGAGAGAATTTTCCTG
      Q   K   C   T   V   S   G   W   G   T   V   T   S   P   R   E   N   F   P   D
1021 ACACTCTCAACTGTGCAGAAGTAAAAATCTTTCCCCAGAAGAAGTGTGAGGATGCTTACC
      T   L   N   C   A   E   V   K   I   F   P   Q   K   K   C   E   D   A   Y   P
1081 CGGGGCAGATCACAGATGGCATGGTCTGTGCAGGCAGCAGCAAAGGGGCTGACACGTGCC
      G   Q   I   T   D   G   M   V   C   A   G   S   S   K   G   A   D   T   C   Q
1141 AGGGCGATTCTGGAGGCCCCCTGGTGTGTGATGGTGCACTCCAGGGCATCACATCCTGGG
      G   D   S   G   G   P   L   V   C   D   A   L   Q   G   I   T   S   W   G
1201 GCTCAGACCCCTGTGGGAGGTCCGACAAACCTGGCGTCTATACCAACATCTGCCGCTACC
      S   D   P   C   G   R   S   D   K   P   G   V   Y   T   N   I   C   R   Y   L
1261 TGGACTGGATCAAGAAGATCATAGGCAGCAAGGGCTGATTCTAGGATAAGCACTAGATCT
      D   W   I   K   K   I   I   G   S   K   G   *   SEQ ID No. 7
1321 CCCTTAATAAACTCACAACTCTC   SEQ ID No. 6
```

Fig. 10A

```
hHk2      --------MW  FLVLCHALSL  GGTGAAPPIQ  SRIVGGWECE  QHSQPWQAAL   42
hPSA      --------MW  VPVVFLTLSV  TWIGAAPLIL  SRIVGGWECE  KHSQPWQVLV   42
mNeur     MGRPPPCAIQ  PWILLLLFMG  AWAGLTRAQG  SKILEGRECI  PHSQPWQAAL   50
hTADG14   MGRPRPRAAK  TWMFLLLLGG  AWAGHSRAQE  DKVLGGHECQ  PHSQPWQAAL   50
hProM     ~~~~~~~MKK  LMVVISLIAA  AWA....EEQ  NKLVHGGPCD  KTSHPYQAAL   39
                                     Y
hHk2      YHFSTFQCGG  ILVHRQWVLT  AAHCISDNYQ  LWLGRHNLFD  DENTAQFVHV   92
hPSA      ASRGRAVCGG  VLVHPQWVLT  AAHCIRNKSV  ILLGRHSLFH  PEDTGQVFQV   92
mNeur     FQGERLICGG  VLVGDRWVLT  AAHCKKQKYS  VRLGDHSLQS  RDQPEQEIQV  100
hTADG14   FQGQQLLCGG  VLVGGNWVLT  AAHCKKPKYT  VRLGDHSLQN  KDGPEQEIPV  100
hProM     YTSGHLLCGG  VLIHPLWVLT  AAHCKKPNLQ  VFLGKHNLRQ  RESSQEQSSV   89
                                     Y
hHk2      SESFPHPGFN  MSLLENHTRQ  ADEDYSHDLM  LLRLTEPADT  ITDAVKVVEL  142
hPSA      SHSFPHPLYD  MSLLKNRFLR  PGDDSSHDLM  LLRLSEPAE.  LTDAVKVMDL  141
mNeur     AQSIQHPCYN  NS........  NPEDHSHDIM  LIRLQNSAN.  IGDKVKPVQL  141
hTADG14   VQSIPHPCYN  SS........  DVEDHNHDLM  LLQLRDQAS.  LGSKVKPISL  141
hProM     VRAVIHPDY.  ..........  DAASHDQDIM  LIRLARPAK.  LSELIQPLPL  127 hHk2      PTQEPEVGST  CLASGWGSIE  PENFSFPDDL  QCVDLKLLPN  DECEKAHVQK  192
hPSA      PTQEPALGTT  CYASGWGSIE  PEEFLTPKKL  QCVDLHVISN  DVCAQVHPQK  191
mNeur     ANLCPKVGQK  CIISGWGTVT  SPQENFPNTL  NCAEVKIYSQ  NKCERAYPGK  191
hTADG14   ADHCTQPGQK  CTVSGWGTVT  SPRENFPDTL  NCAEVKIFPQ  KKCEDAYPGQ  191
hProM     ERDCSANTTS  CHILGWGKTA  D..GDFPDTI  QCAYIHLVSR  EECEHAYPGQ  175
                                     Y
hHk2      VTDFMLCVGH  LEGGKDTCVG  DSGGPLMCDG  VLQGVTSWGY  VPCGTPNKPS  242
hPSA      VTKFMLCAGR  WTGGKSTCSG  DSGGPLVCNG  VLQGITSWGS  EPCALPERPS  241
mNeur     ITEGMVCAGS  SN.GADTCQG  DSGGPLVCDG  MLQGITSWGS  DPCGKPEKPG  240
hTADG14   LTDGMVCAGS  SK.GADTCQG  DSGGPLVCDG  ALQGITSWGS  DPCGRSDKPG  240
hProM     ITQNMLCAGD  EKYGKDSCQG  DSGGPLVCGD  HLRGLVSWGN  IPCGSKEKPG  225 hHk2      VAVRVLSYVK  WIEDTIAENS  SEQ ID No. 11                        262
hPSA      LYTKVVHYRK  WIKDTIVANP  SEQ ID No. 12                        261
mNeur     VYTKICRYTT  WIKKIMDNRD  SEQ ID No. 10                        260
hTADG14   VYTNICRYLD  WIKKILGSKG  SEQ ID No.  7                        260
hProM     VYTNVCRYTN  WIQKTIQAK-  SEQ ID No. 13                        244
```

Fig. 10B

EXTRACELLULAR SERINE PROTEASE

CROSS-REFERENCE TO RELATED APPLICATIONS

This is a divisional application of continuation-in-part application U.S. Ser. No. 09/137,944, filed Aug. 21, 1998, now U.S. Pat. No. 7,067,250, which is a continuation-in-part application of U.S. Ser. No. 08/915,659, filed Aug. 21, 1997, now U.S. Pat. No. 7,014,993.

BACKGROUND OF THE INVENTION

1. Field of the Invention

The present invention relates generally to the fields of cellular biology and the diagnosis of neoplastic disease. More specifically, this invention relates to a novel extracellular serine protease termed Tumor Antigen Derived Gene-14 (TADG-14).

2. Description of the Related Art

Extracellular proteases have been directly associated with tumor growth, shedding of tumor cells and invasion of target organs. Individual classes of proteases are involved in, but not limited to (1) the digestion of stroma surrounding the initial tumor area, (2) the digestion of the cellular adhesion molecules to allow dissociation of tumor cells; and (3) the invasion of the basement membrane for metastatic growth and the activation of both tumor growth factors and angiogenic factors.

The prior art is deficient in the lack of effective means of screening to identify proteases overexpressed in carcinoma. The present invention fulfills this longstanding need in the art.

SUMMARY OF THE INVENTION

The present invention discloses a screening system to identify proteases overexpressed in carcinoma by examining PCR products amplified from early-stage tumors, metastatic tumors, and normal ovarian epithelium.

In one embodiment of the present invention, there is provided a DNA encoding a TADG-14 protein selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein.

In another embodiment of the present invention, there is provided a vector capable of expressing the DNA of the present invention adapted for expression in a recombinant cell and regulatory elements necessary for expression of the DNA in the cell.

In yet another embodiment of the present invention, there is provided a host cell transfected with the vector of the present invention where the vector expresses a TADG-14 protein.

In still another embodiment of the present invention, there is provided a method of detecting expression of a TADG-14 mRNA, comprising the steps of: (a) contacting mRNA obtained from the cell with the labeled hybridization probe; and (b) detecting hybridization of the probe with the mRNA.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows a comparison of the amino acid sequence of TADG-14's catalytic domains.

FIG. 6 shows the complete sequence of the TADG-14 transcript including the open reading frame and common domains.

FIGS. 7A-7B show the homology of TADG-14 with mouse neuropsin. There was approximately 76% identity for the open reading frame and low homology outside of the open reading frame.

FIG. 8 shows the amino acid homology of TADG-14 with mouse neuropsin.

In FIG. 9A messenger RNA was isolated from the tissues of interest and subjected to Northern hybridization using a random labeled 230 bp TADG-14 specific RT-PCR product. The blot was stripped and probed for b-tubulin. In FIGS. 9B-9D multiple tissue Northern blots (Clontech) were probed with the same TADG-14 and b-tubulin specific RT-PCR products. TADG-14 mRNA was detected as a 1.4-kb transcript in tumors and was not detected in any normal tissue studied.

FIGS. 10A-10B show the cDNA and deduced amino acid sequences of TADG-14 and comparison of predicted TADG-14 sequence with known proteases. The cDNA sequence of TADG-14 is shown with its deduced 260 amino acid sequence represented by the one-letter code for each residue. Within the cDNA, the underlined portions represent the Kozak's consensus sequence for initiation of translation and the polyadenylation signal, respectively. The TADG-14 protein sequence contains a secretion signal sequence near its amino terminus (shaded green). The critical residues of the catalytic triad are identified by yellow shading while a potential glycosylation site is marked with purple shading. The stop codon is represented by the (*) symbol. Using the GCG PILEUP program (REF), the amino acid sequence of TADG-14 was compared to human glandular kallikrein (hHk2, accession # P06870), human PSA (hPSA, accession # P07288), mouse neuropsin (mNeur, accession # D30785) and human Protease M (hProM, accession # U62801). Amino acid residues that are identical in at least three of the five sequences are shaded in green. Those residues shaded in yellow represent amino acids that are similar among at least three sequences. The positions of the residues of the catalytic triad are marked.

(FIG. 11B) As determined by the student's t test, TADG-14 mRNA expression levels were significantly elevated in LMP tumors (*, P=0.05) and carcinomas (P<0.0001) compared to levels found in normal ovary. Individual cases are represented in a scatter plot. This is indicative of heterogeneity of TADG-14 expression among these tumor samples.

DETAILED DESCRIPTION OF THE INVENTION

Figure 1:
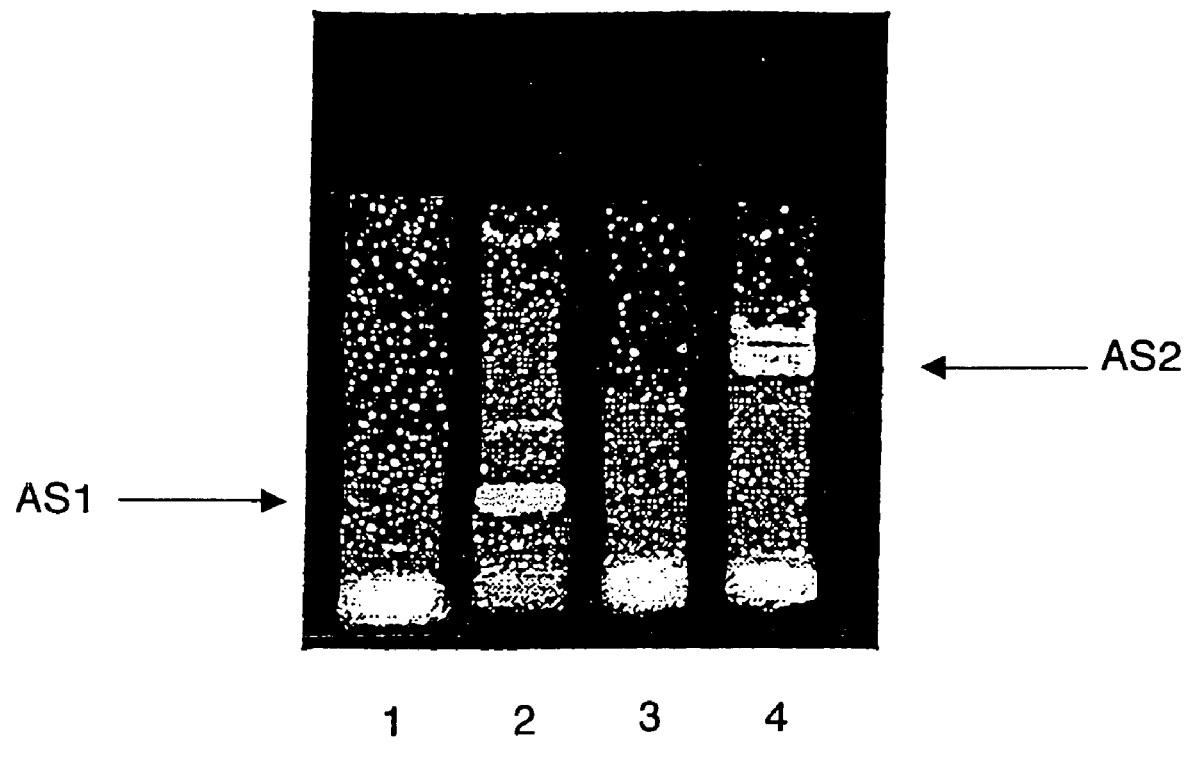
FIG. 1 shows a comparison of PCR products derived from normal and carcinoma cDNA as shown by staining in an agarose gel. Two distinct bands (lane 2) were present in the primer pair sense-His-antisense Asp (AS1) and multiple bands of about 500 base pairs are noted in the carcinoma lane for the sense-His antisense-Ser (AS2) primer pairs (lane 4).

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The TADG-14 cDNA is 1343 base pairs long (SEQ ID NO: 6) and encodes a 260 amino acid protein (SEQ ID NO: 7). The availability of the TADG-14 gene opens the way for a number of studies that can lead to various applications. For example, if the TADG-14 gene underlies a specific human genetic disease, the cDNA can be the basis for a diagnostic predictive test.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. Abbreviations for amino acids may be used in keeping with standard polypeptide nomenclature, *J. Biol. Chem.*, 243:3552-59 (1969) as shown in the following Table of Correspondence.

| 1 Letter Symbol | 3-Letter Abbreviation | Amino Acid Name |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagines |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element, e.g., plasmid, chromosome, or virus, that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides, adenine, guanine, thymine, or cytosine, in its either single-stranded form, or a double-stranded helix. This term refers only to the primary and secondary structure of the molecule and does not limit it to any particular tertiary forms. Thus, this term includes double-stranded DNA found, inter alia, in linear DNA molecules, e.g., restriction fragments, viruses, plasmids, and chromosomes. The structures herein are discussed according to the normal convention of giving only the sequence in the 5' to 3' direction along the nontranscribed strand of DNA, i.e., the strand having a sequence homologous to the mRNA, is applied.

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' amino terminus and a translation stop codon at the 3' carboxyl terminus. A coding sequence can include, but is not limited to, prokaryotic sequences, cDNA from eukaryotic mRNA, genomic DNA sequences from eukaryotic, e.g., mammalian, DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream, i.e., 3' direction, coding sequence. For purposes of defining the present invention, the promoter sequence is bounded at its 3' terminus by the transcription initiation site and extends upstream, i.e., 5' direction, to include the minimum number of bases or elements necessary to initiate transcription at levels detectable above background. Within the promoter sequence will be found a transcription initiation site, as well as protein binding domains or consensus sequences responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide N-terminal to the polypeptide that communicates to the host cell to direct the polypeptide to the cell surface or secrete the polypeptide into the media. This signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprising two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75%, preferably at least about 80% and most preferably at least about 90% or 95%, of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature, e.g., a cDNA where the genomic coding sequence contains introns, or synthetic sequences having codons different than the native gene. Allelic variations or naturally occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $_{-}^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, b-glucuronidase, b-D-glucosidase, b-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human TADG-14 protein of the present invention can be used to transform a host using any of the techniques commonly known to those of ordinary skill in the art. Especially preferred is the use of a vector containing coding sequences for the gene which encodes a human TADG-14 protein of the present invention for purposes of prokaryote transformation.

Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a TADG-14 protein, a strand of which DNA will hybridize at high stringency to a probe containing a sequence of at least 15 consecutive nucleotides of SEQ ID NO: 6. The protein encoded by the DNA of this invention may share at least 80% sequence identity, preferably 85%, more preferably 90%, and most preferably 95%, with the amino acids listed in FIG. 6 for SEQ ID NO: 7. More preferably, the DNA includes the coding sequence of the nucleotides of FIG. 6 in SEQ ID NO:6, or a degenerate variant of such a sequence.

The probe to which the DNA of the invention hybridizes preferably consists of a sequence of at least 20 consecutive nucleotides, more preferably 40 nucleotides, even more preferably 50 nucleotides, and most preferably 100 nucleotides or more up to 100% of the coding sequence of the nucleotides listed in FIG. 6 in SEQ ID NO: 6 or the complement thereof. Such a probe is useful for detecting expression of TADG-14 in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides, preferably 20, more preferably 30, even more preferably 50, and, most preferably all, of the region from nucleotides 1 to 1343 of the nucleotides listed in FIG. 6 in SEQ ID NO: 6.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation, i.e., partial or total purification, of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule, e.g., a cDNA or a genomic or cDNA fragment produced by polymerase chain reaction (PCR) or restriction endonuclease digestion, independent of other sequences. It also includes a recombinant DNA which is part of a hybrid gene encoding additional polypeptide sequence, e.g., a fusion protein. Also included is a recombinant DNA which includes a portion of the nucleotides listed in FIG. 6 in SEQ ID NO: 6 which encodes an alternative splice variant of TADG-14.

The DNA may have at least about 70% sequence identity to the coding sequence of the nucleotides listed in FIG. 6 in SEQ ID NO: 6, preferably at least 75%, e.g. at least 80%, and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10 nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software, e.g., Sequence Analysis Software Package of the Genetics Computer Group, University of Wisconsin Biotechnology Center, 1710 University Avenue, Madison, Wis. 53705.

The present invention comprises a vector comprising a DNA sequence coding for a which encodes a human TADG-14 protein and the vector is capable of replication in a host which comprises, in operable linkage: a) an origin of replication; b) a promoter; and c) a DNA sequence coding for the protein. Preferably, the vector of the present invention contains a portion of the DNA sequence shown in SEQ ID NO: 6. A "vector" may be defined as a replicable nucleic acid construct, e.g., a plasmid or viral nucleic acid. Vectors may be used to amplify and/or express nucleic acid encoding TADG-14 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally occurring organic molecules with which it is naturally associated in vivo. Preferably, the purity of the preparation is at least 75%, more preferably at least 90%, and most preferably at least 99%, by weight. A substantially pure TADG-14 protein may be obtained, for example, by extraction from a natural source; by expression of a recombinant nucleic acid encoding an TADG-14 polypeptide or by chemically synthesizing the protein. Purity can be measured by any appropriate method, e.g., column chromatography, such as immunoaffinity chromatography, using an antibody specific for TADG-14, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments, e.g., antigenic fragments, of the TADG-14 protein in SEQ ID NO: 7. As used herein, "fragment," as applied to a polypeptide, will ordinarily be at least 10 residues, more typically at least 20 residues, and preferably at least 30,e.g., 50, residues in length, but less than the entire, intact sequence. Fragments of the TADG-14 protein can be generated by methods known to those skilled in the art, e.g., by enzymatic digestion of naturally occurring or recombinant TADG-14 protein, by recombinant DNA techniques using an expression vector that encodes a defined fragment of TADG-14, or by chemical synthesis. The ability of a candidate fragment to exhibit a characteristic of TADG-14, e.g., binding to an antibody specific for TADG-14, can be assessed by methods described herein. Purified TADG-14 or antigenic fragments of TADG-14 can be used to generate new antibodies or to test existing antibodies, e.g., as positive controls in a diagnostic assay, by employing standard protocols known to those skilled in the art. Included in this invention are polyclonal antisera generated by using TADG-14 or a fragment of TADG-14 as the immunogen in, e.g., rabbits. Standard protocols for monoclonal and polyclonal antibody production known to those skilled in this art are employed. The monoclonal antibodies generated by this procedure can be screened for the ability to identify recombinant TADG-14 cDNA clones, and to distinguish them from known cDNA clones.

Further included in this invention are TADG-14 proteins which are encoded at least in part by portions of SEQ ID NO: 7, e.g., products of alternative mRNA splicing or alternative protein processing events, or in which a section of TADG-14 sequence has been deleted. The fragment, or the intact TADG-14 polypeptide, may be covalently linked to another polypeptide, e.g. which acts as a label, a ligand or a means to increase antigenicity.

The invention also includes a polyclonal or monoclonal antibody which specifically binds to TADG-14. The invention encompasses not only an intact monoclonal antibody, but also an immunologically-active antibody fragment, e.g., a Fab or (Fab)$_2$ fragment, an engineered single chain Fv molecule or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or calorimetric label. Examples of suitable toxins include diphtheria toxin, *Pseudomonas* exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472-480; Shreve et al., (1986) *Magn. Reson. Med.* 3, 336-340; Wolf, G. L., (1984) *Physiol. Chem. Phys. Med. NMR* 16, 93-95; Wesbey et al., (1984) *Physiol. Chem. Phys. Med. NMR* 16, 145-155; Runge et al., (1984) *Invest. Radiol.* 19, 408-415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) *Clin. Chim. Acta* 70, 1-31; and Schurs et al., (1977) *Clin. Chim. Acta* 81, 1-40. Coupling techniques mentioned in the latter are the glutaraldehyde method, the periodate method, the dimaleimide method, the m-maleimidobenzyl-N-hydroxy-succinimide ester method.

Also within the invention is a method of detecting TADG-14 protein in a biological sample, which includes the steps of contacting the sample with the labeled antibody, e.g., radioactively tagged antibody specific for TADG-14, and determining whether the antibody binds to a component of the sample.

As described herein, the invention provides a number of diagnostic advantages and uses. For example, the TADG-14 protein is useful in diagnosing cancer in different tissues since this protein is absent in highly proliferating cells. Antibodies or antigen-binding fragments thereof which bind to an epitope specific for TADG-14 are useful in a method of detecting TADG-14 protein in a biological sample for diagnosis of cancerous or neoplastic transformation. This method includes the steps of obtaining a biological sample, e.g., cells, blood, tissue, etc., from a patient suspected of having cancer, contacting the sample with a labelled antibody, e.g., radioactively tagged antibody, specific for TADG-14 and detecting the TADG-14 protein using standard immunoassay techniques such as an ELISA. Antibody binding to the biological sample indicates that the sample contains a component which specifically binds to an epitope within TADG-14.

Likewise, a standard Northern blot assay can be used to ascertain the relative amounts of TADG-14 mRNA in a cell or tissue obtained from a patient suspected of having cancer, in accordance with conventional Northern hybridization techniques known to those persons of ordinary skill in the art. This Northern assay uses a hybridization probe, e.g. radiolabeled TADG-14 cDNA, either containing the full-length, single stranded DNA having a sequence complementary to SEQ ID NO: 6 (FIG. 6), or a fragment of that DNA sequence at least 20, preferably at least 30, more preferably at least 50, and most preferably at least 100 consecutive nucleotides in length. The DNA hybridization probe can be labeled by any of the many different methods known to those skilled in this art.

Antibodies to the TADG-14 protein can be used in an immunoassay to detect increased levels of TADG-14 protein expression in tissues suspected of neoplastic transformation. These same uses can be achieved with Northern blot assays and analyses.

The present invention is directed to DNA encoding a TADG-14 protein selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein. Preferably, the DNA has the sequence shown in SEQ ID NO. 6. More preferably, the DNA encodes a TADG-14 protein having the amino acid sequence shown in SEQ ID NO. 7.

The present invention is also directed to a vector capable of expressing the DNA of the present invention adapted for expression in a recombinant cell and regulatory elements necessary for expression of the DNA in the cell. Preferably, the vector contains DNA encoding a TADG-14 protein having the amino acid sequence shown in SEQ ID NO. 7.

The present invention is also directed to a host cell transfected with the vector described herein where the vector expresses a TADG-14 protein. Representative host cells include bacterial cells, mammalian cells and insect cells.

The present invention is also directed to a isolated and purified TADG-14 protein coded for by DNA selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein. Preferably, the isolated and purified TADG-14 protein has the amino acid sequence shown in SEQ ID NO. 7.

The present invention is also directed to a method of detecting expression of the protein described herein, comprising the steps of: (a) contacting mRNA obtained from the cell with the labeled hybridization probe; and (b) detecting hybridization of the probe with the mRNA.

The following examples are given for the purpose of illustrating various embodiments of the invention and are not meant to limit the present invention in any fashion.

Example 1

Tissue Collection and Storage

Upon patient hysterectomy, bilateral salpingo-oophorectomy, or surgical removal of neoplastic tissue, the specimen is retrieved and placed on ice. The specimen was then taken to the resident pathologist for isolation and identification of specific tissue samples. Finally, the sample was frozen in liquid nitrogen, logged into the laboratory record and stored at −80° C. Additional specimens were frequently obtained from the Cooperative Human Tissue Network (CHTN). These samples were prepared by the CHTN and shipped to us on dry ice. Upon arrival, these specimens were logged into the laboratory record and stored at −80° C.

Example 2 mRNA Isolation and cDNA Synthesis

Messenger RNA (mRNA) isolation was performed according to the manufacturer's instructions using the Mini RiboSep™ Ultra mRNA isolation kit purchased from Becton Dickinson (Cat. NO. 30034). This was an oligo(dt) chromatography based system of mRNA isolation. The amount of mRNA recovered was quantitated by UV spectrophotometry.

First strand complementary DNA (cDNA) was synthesized using 5.0 mg of mRNA and either random hexamer or oligo (dT) primers according to the manufacturer's protocol utilizing a first strand synthesis kit obtained from Clontech (Cat. NO. K1402-1). The purity of the cDNA was evaluated by PCR using primers specific for the p53 gene. These primers span an intron such that pure cDNA can be distinguished from cDNA that is contaminated with genomic DNA.

Example 3

PCR Reactions

Reactions were carried out as follows: first strand cDNA generated from 50 ng of mRNA will be used as template in the presence of 1.0 mM MgCl2, 0.2 mM dNTPs, 0.025 U Taq polymerase/ml of reaction, and 1× buffer supplied with enzyme. In addition, primers must be added to the PCR reaction. Degenerate primers that may amplify a variety of cDNAs are used at a final concentration of 2.0 mM each, whereas primers which amplify specific cDNAs are added to a final concentration of 0.2 mM each.

After initial denaturation at 95° C. for 3 minutes, thirty cycles of PCR are carried out in a Perkin Elmer Gene Amp 2400 thermal cycler. Each cycle consists of 30 seconds of denaturation at 95° C., 30 seconds of primer annealing at the appropriate annealing temperature*, and 30 seconds of extension at 72° C. The final cycle will be extended at 72° C. for 7 minutes. To ensure that the reaction succeeded, a fraction of the mixture will be electrophoresed through a 2% agarose/TAE gel stained with ethidium bromide (final concentration 1 mg/ml). The annealing temperature varies according to the primers that are used in the PCR reaction. For the reactions involving degenerate primers, an annealing temperature of 48° C. were used. The appropriate annealing temperature for the TADG-14 and b-tubulin specific primers is 62° C.

Example 4

T-Vector Ligation and Transformations

The purified PCR products are ligated into the Promega T-vector plasmid and the ligation products are used to transform JM109 competent cells according to the manufacturer's instructions (Promega Cat. NO. A3610). Positive colonies were cultured for amplification, the plasmid DNA isolated by means of the Wizard™ Minipreps DNA purification system (Promega cat #A7500), and the plasmids were digested with ApaI and SacI restriction enzymes to determine the size of the insert. Plasmids with inserts of the size(s) visualized by the previously described PCR product gel electrophoresis were sequenced.

Example 5

DNA Sequencing

Utilizing a plasmid specific primer near the cloning site, sequencing reactions were carried out using PRISM™ Ready Reaction Dye Deoxy™ terminators (Applied Biosystems Cat. NO. 401384) according to the manufacturer's instructions. Residual dye terminators were removed from the completed sequencing reaction using a Centri-sep™ spin column (Princeton Separation Cat. NO. CS-901). An Applied Biosystems Model 373A DNA Sequencing System was available and was used for sequence analysis. Based upon the determined sequence, primers that specifically amplify the gene of interest were designed and synthesized.

Example 6

Northern Blot Analysis mRNAs (approximately 5 mg) were size separated by electrophoresis through a 6.3% formaldehyde, 1.2% agarose gel in 0.02 M MOPS, 0.05 M sodium acetate (pH 7.0), and 0.001 M EDTA. The mRNAs were then blotted to Hybond-N (Amersham) by capillary action in 20×SSPE. The RNAs are fixed to the membrane by baking for 2 hours at 80° C. Additional multiple tissue northern (MTN) blots were purchased from CLONTECH Laboratories, Inc. These blots include the Human MTN blot (Cat. NO. 7760-1), the Human MTN II blot (Cat. NO. 7759-1), the Human Fetal MTN II blot (Cat. NO. 7756-1), and the Human Brain MTN III blot (Cat. NO. 7750-1). The appropriate probes were radiolabeled utilizing the Prime-a-Gene Labelling System available from Promega (cat #U1100). The blots were probed and stripped according to the ExpressHyb Hybridization Solution protocol available from CLONTECH (Cat. Nos. 8015-1 or 8015-2).

Example 7

Quantitative PCR

Quantitative-PCR was performed in a reaction mixture consisting of cDNA derived from 50 ng of mRNA, 5 pmol of sense and antisense primers for TADG-14 and the internal control β-tubulin, 0.2 mmol of dNTPs, 0.5 mCi of [α-$^{32}$P] dCTP, and 0.625 U of Taq polymerase in 1× buffer in a final volume of 25 ml. This mixture was subjected to 1 minute of denaturation at 95° C. followed by 30 cycles of denaturation for 30 seconds at 95° C., 30 seconds of annealing at 62° C., and 1 minute of extension at 72° C. with an additional 7 minutes of extension on the last cycle. The product was electrophoresed through a 2% agarose gel for separation, the gel was dried under vacuum and autoradiographed. The relative radioactivity of each band was determined by PhosphoImager from Molecular Dynamics.

Example 8

Primers

The present invention describes the use of primers directed to conserved areas of the serine protease class to identify members of that class which are overexpressed in carcinoma. Several genes were identified and cloned in other tissues, but not previously associated with ovarian carcinoma. The present invention describes a novel protease identified in ovarian carcinoma. This gene was identified using primers to the conserved area surrounding the catalytic domain amino acid histidine and the catalytic domain amino acid serine which is about 150 amino acids downstream towards the carboxyl end.

The gene encoding the novel extracellular serine protease of the present invention was identified from a group of proteases overexpressed in carcinoma by subcloning and sequencing the appropriate PCR products. An example of such a PCR reaction is given in FIG. 1. Subcloning and sequencing of individual bands from such amplification provided a basis for identifying the novel protease of the present invention.

Example 9

Expression of TADG-14 Protein

The sequence determined for the catalytic domain of TADG-14 is presented in FIG. 2 and is consistent with other serine proteases and specifically contains conserved amino acids appropriate for the catalytic domain of the serine protease family. Specific primers (20mers) derived from this sequence were used.

Figure 3:
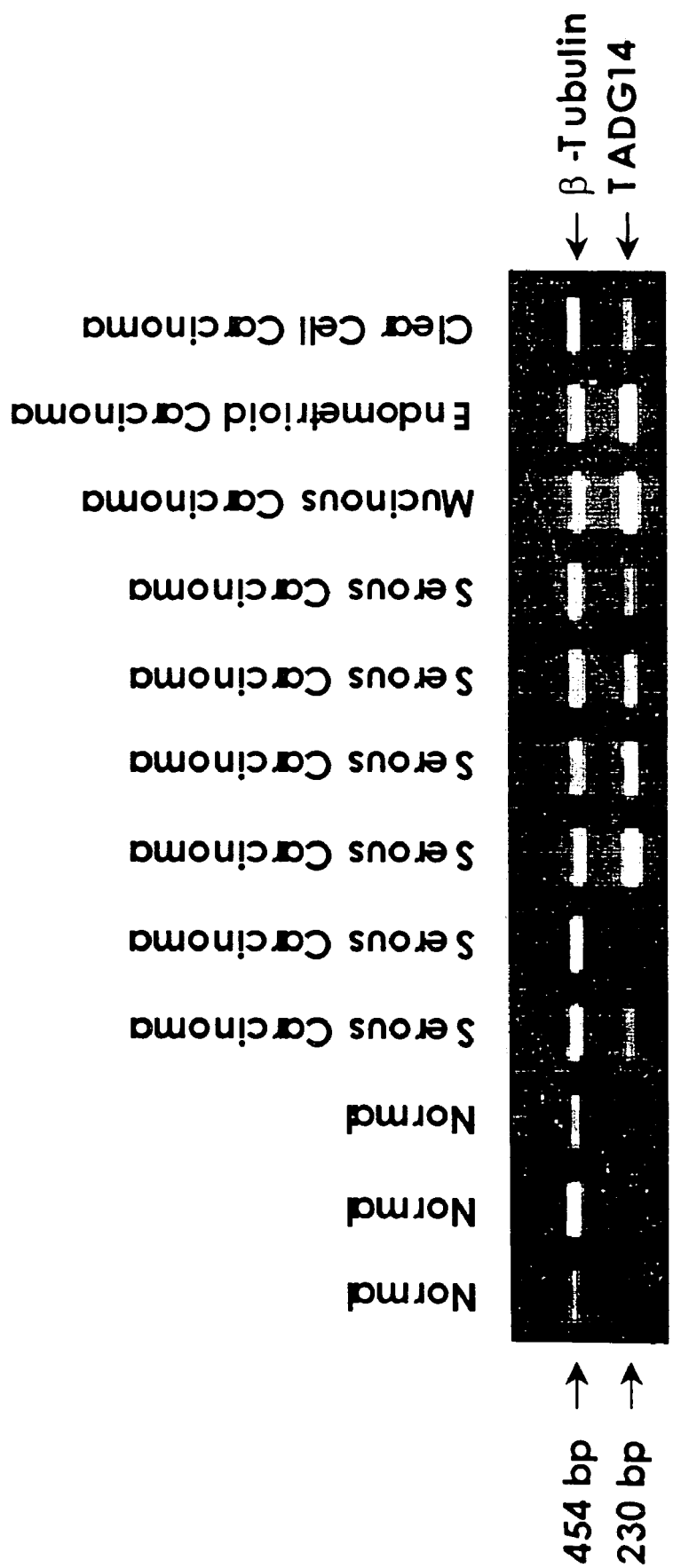
FIG. 3 shows the overexpression of TADG-14 in ovarian carcinomas.
Figure 4:
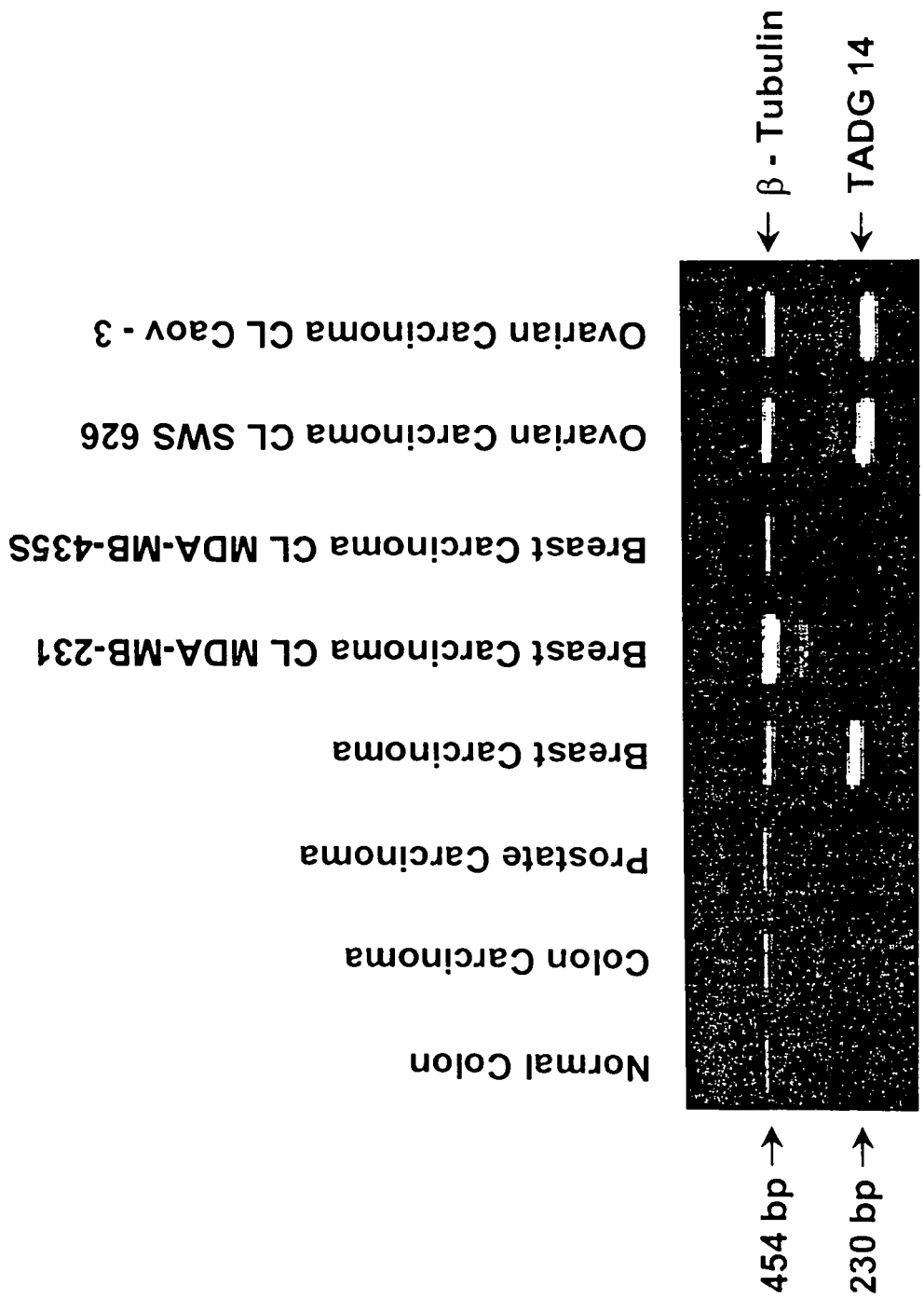
FIG. 4 shows the TADG-14 expression in tumors and cell lines.

A series of normal and tumor cDNAs were examined to determine the expression of the TADG-14 protein. In a series of three normals compared to nine carcinomas using b-tubulin as an internal control for PCR amplification, TADG-14 was significantly overexpressed in eight of the nine carcinomas and either was not detected or was detected at a very low level in normal epithelial tissue (FIG. 3). This evaluation was extended to a standard panel of about 35 tumors. Using these specific primers, the expression of this gene was also examined in both tumor cell lines and other tumor tissues as shown in FIG. 4. The expression of TADG-14 was also observed in breast carcinoma and colon carcinoma. TADG-14 expression was not noted in other tissues. For example, TADG-14 was not present in detectable levels by Northern blot analysis in any of the following normal tissues: fetal lung, fetal heart, fetal brain, fetal kidney, adult spleen, thymus, prostate, testis, ovary, small intestine, colon, peripheral blood leukocytes, heart, placenta, lung, liver, skeletal muscle, kidney, pancreas, amygdala, caudate nucleus, corpus callosum, hippocampus, whole brain, subthalamic nucleus and thalamus.

Figure 5:
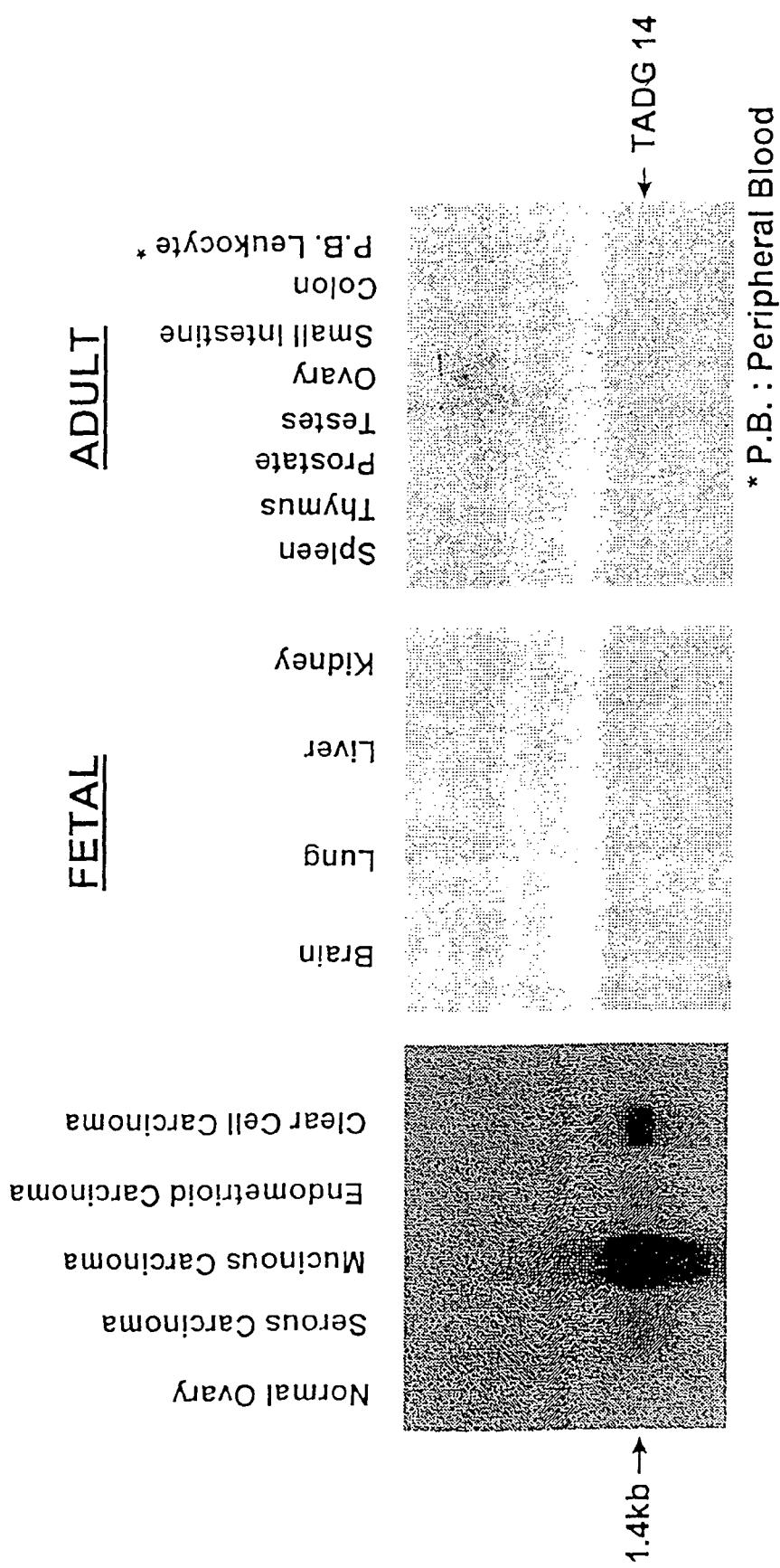
FIG. 5 shows the blots of TADG-14 expression in fetal, adult and ovarian carcinoma tissues.

Using the specific sequence for TADG-14 covering the full domain of the catalytic site as a probe for Northern blot analysis, three Northern blots were examined: one derived from ovarian tissues, both normal and carcinoma; one from fetal tissues; and one from adult normal tissues. As noted in FIG. 5, abundant transcripts for TADG-14 were noted in ovarian carcinomas. Transcripts were noted in all carcinomas, but at lower levels in some sub-types of ovarian cancer. Furthermore, no transcript was observed from normal ovarian tissue. The transcript size was found to be approximately 1.4 kb. Of particular note is the fact that in the fetal tissue examined including brain, lung, liver, kidney and in multiple adult tissues examined, none of these blots showed expression for the TADG-14 transcript. The hybridization for the fetal and adult blots was appropriate and done with the same probe as with the ovarian tissue. Subsequent to this examination, it was confirmed that these blots contained other detectable mRNA transcripts Using the base sequence derived from the original full-length PCR clone corresponding to nucleotides 713-1160 of the catalytic domain as a probe to screen libraries, an ovarian carcinoma library derived from ascites tumor cells was examined for the presence of TADG-14. Four clones were obtained, two of which covered the complete mRNA 1.4 kb transcript of the TADG-14 gene. The complete nucleotide sequence of SEQ ID NO: 6 is provided in FIG. 6 along with translation of the open reading frame as SEQ ID NO: 7.

In the nucleotide sequence, there is a Kozak sequence typical of sequences upstream from the initiation site of translation. There is also a polyadenylation signal sequence and a poly-A tail. The open reading frame consists of a 260 amino acid sequence (SEQ ID NO: 7) which includes a secretion signal sequence in the first 25 amino acids confirming the extracellular processing of the protease. Also a clear delineation of the catalytic domain conserved histidine, aspartic acid, serine series along with a series of amino acids conserved in the serine protease family is indicated.

Examination of the databases for both the expressed tag sequence and complete transcripts provided seven genes that had significant homology to this newly identified serine protease. One gene was identified from mouse brain and a comparison of the nucleotide homology is provided in FIGS. 7A-7B. A comparison of the homology of the amino acid sequence is provided in FIG. 8. Alignment of TADG-14 with mouse neuropsin revealed 77.2% similarity and 72.2% identity at the amino acid levels for these two genes. Given that the size of the mouse transcript is 1.4 kb and that the mouse gene contains 260 amino acids and there is greater than 70% homology, this gene may be a human equivalent of the mouse neuropsin gene or a member of neuropsin-like genes.

TADG-14 is secreted and expressed early in tumor development and has invasive capacity. TADG-14 therefore is a potential diagnostic for ovarian and other cancers. TADG-14 also may be a target for intervention in regulating tumor spread by inhibition, gene therapy, or antibody inactivation technology. In addition to its obvious usefulness in ovarian carcinoma and other carcinomas including the preliminary data on breast and prostate, the neuropsin-like qualities may provide an opportunity for usefulness in neuropathologic disorders.

Example 10

Identification of Expressed Serine Proteases

To identify the expressed serine proteases, degenerate oligodeoxynucleotide primers designed to the conserved amino acid sequences surrounding the invariant His and Ser residues of the catalytic triad were used in PCR reactions with cDNA from either normal ovarian tissue or ovarian carcinoma as the template. PCR products of the appropriate size were subcloned into T-vector and sequenced. Proteases already identified using this strategic approach, e.g. hepsin and stratum corneum chymotryptic enzyme (SCCE), have been expressed at abnormally high levels in ovarian carcinoma. Homology searches for this novel protease TADG-14 revealed that one of the subclones obtained from ovarian carcinoma represented a novel 406 base pair (bp) sequence that has significant sequence similarity to other known proteases including mouse neuropsin, human glandular kallikrein and human PSA.

The complete cDNA for this novel sequence was cloned and found to encode a trypsin like serine protease, named TADG-14. More importantly, the TADG-14 transcript was highly expressed in a majority of ovarian tumors but not expressed by normal ovarian tissue. High-level expression of TADG-14 appears to be restricted to tumors, and this protease appears to be secreted in a manner that would suggest a possible role in invasion and metastasis. Moreover, due to the extracellular nature of this enzyme, it may be possible to exploit its expression as a diagnostic tool for ovarian cancer.

Figure 9:
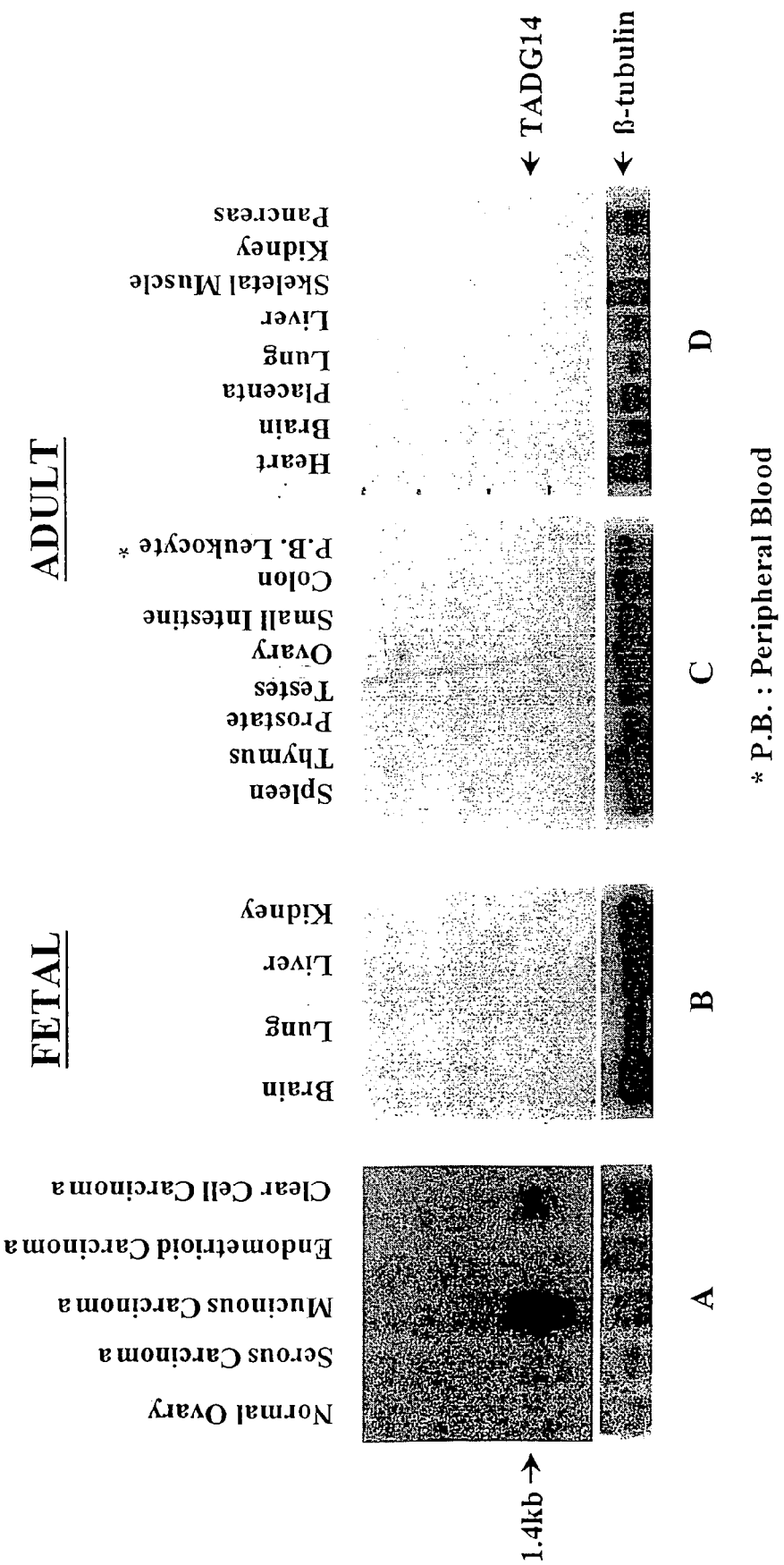
FIGS. 9A-9D show various Northern Blot analyses.

Using the novel 406 bp sequence as a probe, Northern blot analysis was carried out to determine the transcript size and tissue specificity of its expression. It was found that the mRNA for this clone is approximately 1.4 kilobases (kb) (FIG. 9A), and that it is strongly expressed in ovarian carcinomas but not in normal ovary. More importantly, the transcript was found to be undetectable by Northern analysis in 28 normal human tissues studied (FIGS. 9B, 9C, 9D some data not shown). In a more sensitive assay of 50 normal human tissues (Clontech) RNA dot blot analysis revealed that this clone was very weakly expressed in only three of these 50 tissues, kidney, lung and mammary gland (data not shown).

Using standard hybridization techniques, a cDNA library constructed from the mRNA isolated from the ascites cells of an ovarian cystadenocarcinoma patient was screened. Five clones were obtained, two of which overlapped and spanned 1343 nucleotides (FIG. 10A). The last two nucleotides prior to the poly (A) tail and the poly (A) tail itself were obtained from the EST database available at NCBI (Accession No. AA343629). Subsequent Northern blot analyses with probes derived from sequences near the 5' or 3' end of this cDNA were consistent with previous results suggesting that the obtained clones were produced by the same gene (data not shown).

This cDNA includes a Kozak's consensus sequence for the initiation of translation, and a polyadenylation signal. The mRNA provides an open reading frame of 260 amino acids, which contains the necessary residues, His73, Asp120 and Ser213, in the appropriate context to classify this protein as a trypsin-like serine protease. Near its amino-terminus, the predicted protein contains a stretch of hydrophobic amino acids that may act as a secretion signal sequence. In addition, residues 110 to 112 encode a potential site for glycosylation that is common to serine proteases of the kallikrein subfamily such as PSA. This enzyme was named TADG-14.

As shown in FIG. 10B comparison of the deduced TADG-14 amino acid sequence with sequences of known proteases revealed that it possesses significant similarity with mouse neuropsin (mNeur; SEQ ID NO: 10), human glandular kallikrein (hHk2; SEQ ID NO: 11), human PSA (hPSA, SEQ ID NO: 12), and Protease M (hProM, SEQ ID NO: 13). At the amino acid level TADG-14 is 48% identical to Protease M, 46% identical to hHk2, and 43% identical to PSA. More interestingly, the mouse protease neuropsin and TADG-14 share 72% amino acid identity. In addition to the similarity of the protein sequences, neuropsin and TADG-14 mRNAs are of similar size (1.4 kb) and structure with approximately the same amounts of 5' and 3' untranslated regions suggesting the possibility of orthology. Neuropsin was originally cloned from mouse hippocampus and is differentially expressed under stimulation. However, TADG-14 mRNA was undetectable in human hippocampus by Northern blot (data not shown). Nucleotide sequences of mouse neuropsin and TADG-14 are shown in SEQ ID NO: 8 and SEQ ID NO: 9.

To characterize the extent and frequency of expression of the TADG-14 gene in ovarian tumors quantitative PCR was utilized with cDNA derived from normal ovary, ovarian carcinoma or low malignant potential (LMP) tumors as template. This technique has been previously authenticated and verified by Northern blot and Western blot. PCR primers that amplify a TADG-14 specific 230 bp product were synthesized and used simultaneously in reactions with primers that produce a specific 454 bp PCR product for β-tubulin. For TADG-14 specific PCR the primers were: sense, 5'-ACAGTACGC-CTGGGAGACCA-3' (SEQ ID NO: 14); antisense, 5'-CT-GAGACGGTGCMTTCTGG-3' (SEQ ID NO: 15). The tubulin primers were as described in ref. 11.

Figure 11A:
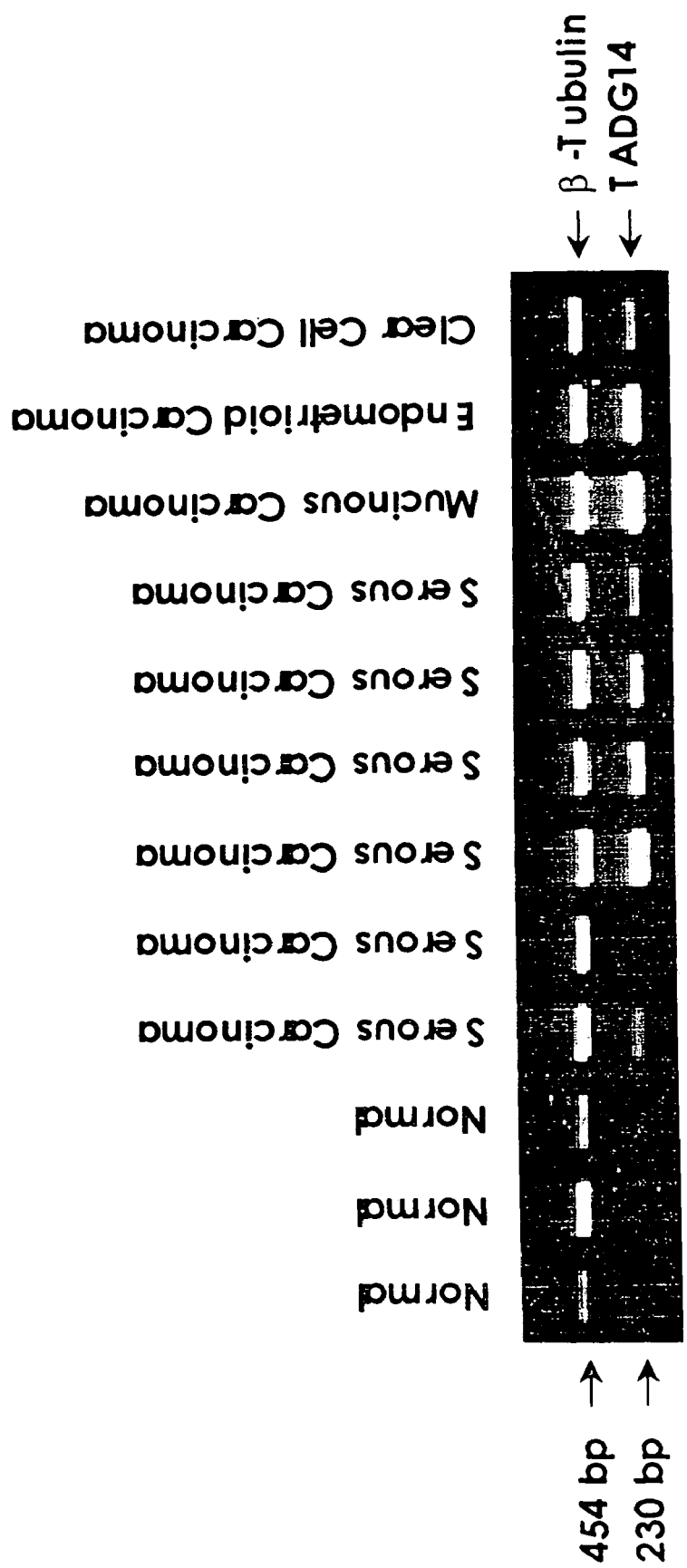
FIGS. 11A-11B show the TADG-14 quantitative PCR. Typical results of a TADG-14 quantitative PCR experiment are shown (FIG. 11A). The reaction products were electrophoresed through a 2% agarose TAE gel and stained with ethidium bromide. In this figure, the 454-bp band represents the b-tubulin product and the 230-bp band represents the TADG-14 product. The radiolabeled PCR products were quantitated.

Reactions were carried out as follows: first strand cDNA generated from 50 ng of mRNA was used as template in the presence of 1.0 mM $MgCl_2$, 0.2 mM dNTPs, 0.025 U Taq polymerase/ml of reaction, and 1× buffer supplied with enzyme. Primers which amplify specific cDNAs are added to a final concentration of 0.2 mM each. After initial denaturation at 95 C for 3 minutes, thirty cycles of PCR were carried out in a Perkin Elmer Gene Amp 2400 thermal cycler. Each cycle consists of 30 seconds of denaturation at 95 C, 30 seconds of primer annealing at 62 C and 30 seconds of extension at 72 C. The final cycle was extended at 72 C for 7 minutes. A radiolabelled nucleotide was included in this reaction, the PCR products were separated on a 2% agarose gel and the intensity of each band was quantitated by a Phosphoimager (Molecular Dynamics). FIG. 11A shows an ethidium bromide stained agarose gel with the separated quantitative PCR products and is representative of the typical results observed.

Figure 11B:
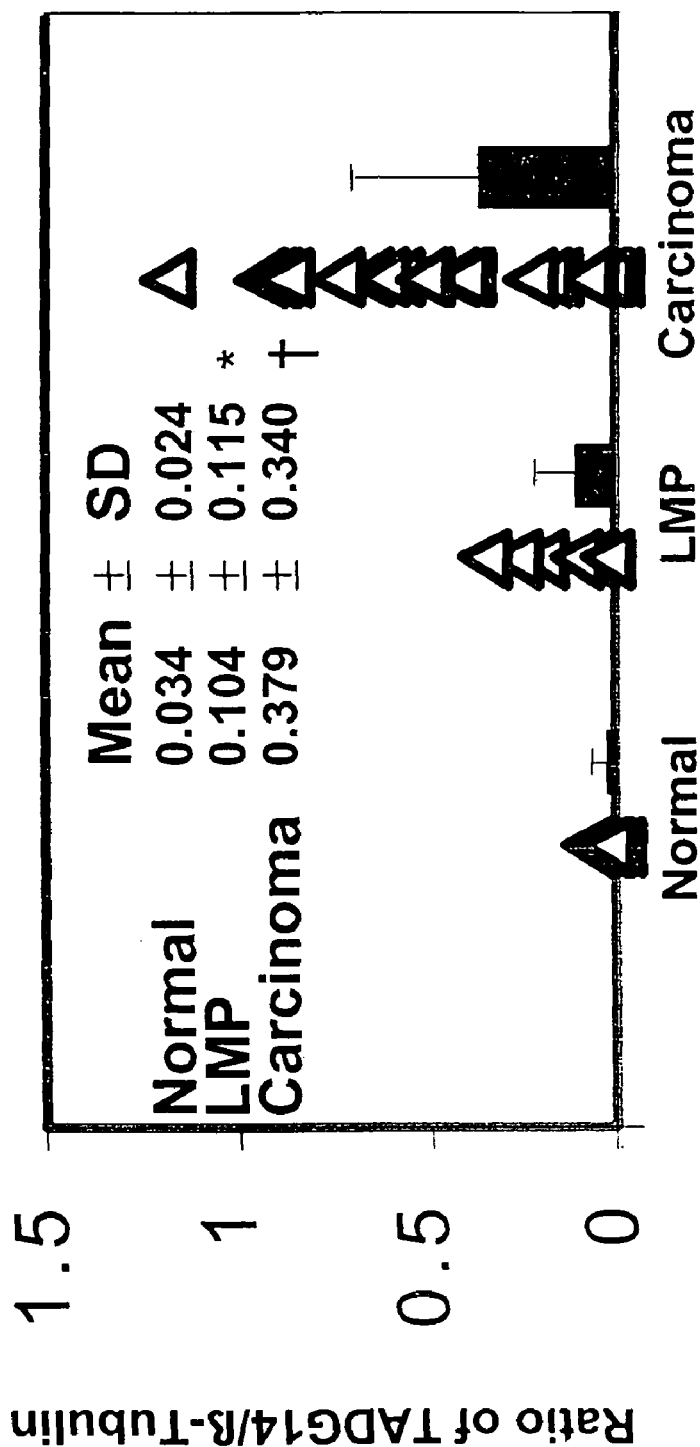

The ratio of the TADG-14 PCR product to that of β-tubulin (mean±SD) was calculated for normal ovary (0.034±0.024) samples which all showed relatively low expression levels. TADG-14 overexpression was defined as exceeding the mean of the ratio of TADG-14 to β-tubulin for normal samples by greater than 2 standard deviations (SD). TADG-14 was overexpressed in 4 of 10 LMP tumors (40%), and 20 of 30 ovarian carcinomas (67%) studied. For individual histologic subtypes of tumor, the expression ratio was 0.110±0.092 for serous LMP tumors, 0.096±0.142 for mucinous LMP tumors, 0.457±0.345 for serous carcinomas, 0.171±0.300 for mucinous carcinomas, 0.308±0.144 for clear cell carcinomas, and 0.485±0.325 for endometrioid carcinomas. Of the 30 carcinomas studied, 13 of 17 serous tumors, 1 of 7 mucinous tumors, 3 of 3 clear cell tumors and 3 of 3 endometrioid tumors overexpressed TADG-14 (FIG. 11B).

Figure 12:
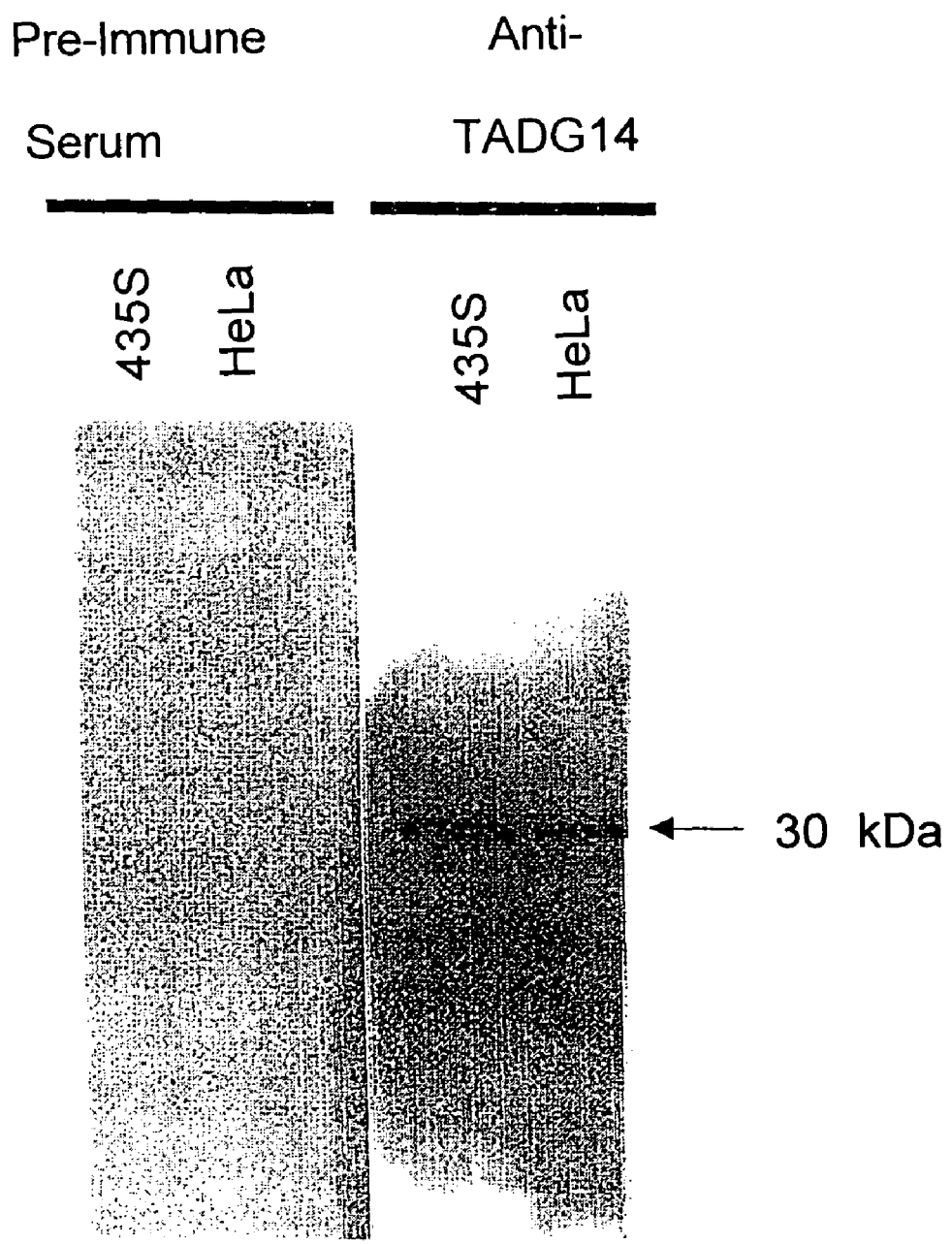
FIG. 12 shows a Western Blot. Polyclonal antibodies were generated by immunization of rabbits with one of three polylysine linked multiple antigen peptides derived from the deduced amino acid sequence of TADG-14. These sequences are KYTVRLGDHSLQ (T14-1; SEQ ID NO: 16), GHECQPHSQPWQ (T14-2; SEQ ID NO: 17), and LDWIKKIIGSKG (T14-3; SEQ ID NO: 18). For Western blot analysis, approximately 20 µg of MDA-MB-435S and HeLa cell lysates were separated on a 15% SDS-PAGE gel and electroblotted to PVDF at 100V for 40 minutes at 4 C. The blot was blocked overnight in Tris-buffered saline (TBS), pH 7.8 containing 0.2% non-fat milk. Primary antibody was added to the membrane at a dilution of 1:100 in 0.2% milk/TBS and incubated for 2 hours at room temperature. The blot was washed and incubated with 1:3000 dilution of alkaline-phosphatase conjugated goat and anti-rabbit IgG antibody (Bio-Rad) for one hour at room temperature. The blot was washed and incubated with a chemiluminescent substrate (Bio-Rad) before a 10-second exposure to X-ray film for visualization.
Figure 13C:
FIGS. 13A-13F show immunohistochemistry. Staining was with the TADG-14-1 antibody for normal ovary, two serous carcinomas, mucinous carcinoma, endometrioid carcinoma and clear cell carcinoma of the ovary (FIGS. 13A, 13B, 13C, 13D, 13E, and 13F, respectively). NO staining was observed in normal ovary. The serous carcinoma shown in FIG. 13B has TADG-14 most strongly associated with the surface of the tumor, while in the serous tumor in FIG. 13C, TADG-14 is found in a granular form in an apparent secretion pathway. In mucinous carcinoma TADG-14 appears to be most highly expressed along the invasive front of the tumor. TADG-14 is secreted into the lumen of the glandular structure formed by the endometrioid carcinoma in FIG. 13E. The clear cell carcinoma stained in FIG. 13F shows diffuse staining throughout all tumor cells.
Figure 13B:
Figure 13A:
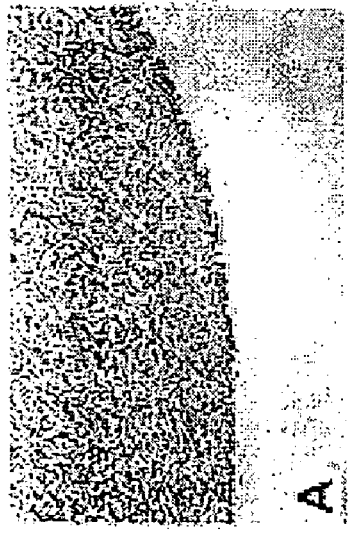
Figure 13F:
Figure 13E:
Figure 13D:
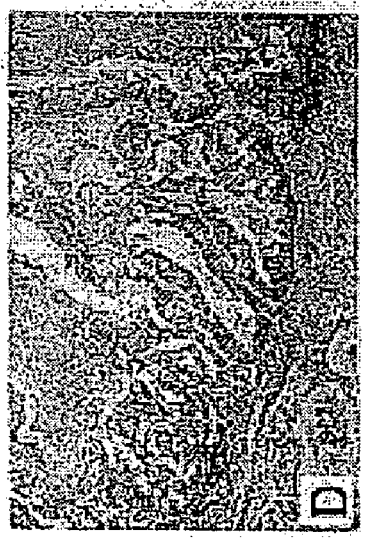

Immunogenic poly-lysine linked multiple antigen peptides (SEQ ID NOS: 16-18) were synthesized based on the deduced amino acid sequence of TADG-14 and used to immunize rabbits for the production of polyclonal antibodies. The antiserum raised to the peptide sequence LDWIKKIIG-SKG (SEQ ID NO: 18) was used in western blot analysis to determine if this antibody would recognize a protein of the predicted size of 28 kDa. Proteins from the cervical cancer derived HeLa cell line and the breast carcinoma derived MD-MBA-435S cell line were used in this experiment and it was found that the antibody recognized a single 30 kDa protein in both (FIG. 12A, lanes 3 and 4). This size is within a reasonable range of the predicted molecular weight. As a negative control, duplicate HeLa and MD-MB435S lysates were examined with rabbit pre-immune serum (FIG. 12A, lanes 1 and 2). More importantly, this experiment was reproducible with antisera to a peptide from a different region of TADG-14, suggesting that cultured cancer cells produce the TADG-14 protein.

Immunohistochemical staining supported the data obtained by quantitative PCR and by Northern blot as shown in FIGS. 13A-13F. Using a TADG-14 peptide directed antibody, no staining was observed with normal ovarian tissue samples. However, intense staining was associated with tumor cells of all of the various histological subtypes of ovarian carcinoma examined. For serous carcinoma, the antigen appears to be associated with tumor cells in the form of granules. These granular structures may be intermediates in the pathway that ultimately leads to secretion of TADG-14. In mucinous and clear cell carcinoma samples, TADG-14 is highly associated with the tumor cells. In endometrioid carcinoma, the antigen is most prevalent in the glandular lumen formed by the tumor cells.

The lethality of cancer cells lies in their ability to proliferate abnormally and invade normal host tissues. Malignancies employ proteases to provide a variety of services that assist in the process of tumor progression including activation of growth and angiogenic factors and to provide the basis for invasion and metastasis. In the process of studying these enzymes, overexpression of the known proteases, hepsin and SCCE was identified. In the present study, a cDNA was cloned encoding a novel serine protease, TADG-14. This protease was found to be very highly expressed in 67% (20/30) of ovarian carcinomas studied, whereas it was undetected in normal ovarian tissue. No detection of the TADG-14 transcript at levels similar to tumor samples in any of 50 normal human tissues studied was made. This suggests the possibility that this gene is under the control of a promoter that is most active in ovarian tumors, and it may be possible to exploit this for therapeutic means.

At the amino acid level, TADG-14 most closely resembles a mouse protease known as neuropsin, which was originally cloned from mouse hippocampus. Neuropsin has been implicated in neuronal plasticity, which suggests that TADG-14 may very well be capable of restructuring the three-dimensional architecture of a tumor allowing for shedding of tumor cells or invasion of normal host tissues. Immunohistochemical staining of ovarian tumors revealed that TADG-14 is highly associated with tumor cells and the cells near the invasive fronts of tumor cells. Therefore, TADG-14 is an important target for the inhibition of tumor progression.

Most importantly, the five-year survival rate for ovarian cancer patients remains below 50% because of an inability to diagnose this disease at an early stage. TADG-14 contains a secretion signal sequence and immunohistochemical data suggest that TADG-14 is secreted. In addition, by Northern blot and RNA dot blot analyses, TADG-14 appears to be rather tumor specific. As a result of this, it may be possible to design assays based on the detection of this protein for the early detection of ovarian cancer. Currently, the best available ovarian cancer tumor marker is CA125. However, due to high endogenous circulating levels of this antigen, the signal to noise ratio limits its usefulness as a diagnostic tool. Therefore, TADG-14, due to its limited expression in other tissues, may prove to be a valuable tool for diagnosing ovarian cancer, especially the most prevalent serous cystadenocarcinoma subtype.

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated and purified Tumor Antigen Derived Gene-14 (TADG-14) protein consisting of SEQ ID NO. 7, wherein said protein is encoded by DNA consisting of SEQ ID NO: 6.

* * * * *

SEQUENCE LISTING

<160> NUMBER OF SEQ ID NOS: 18

<210> SEQ ID NO 1
<211> LENGTH: 144
<212> TYPE: PRT
<213> ORGANISM: unknown
<220> FEATURE:
<221> NAME/KEY: DOMAIN
<223> OTHER INFORMATION: Amino acid sequence of Protease m (Prom)
      catalytic domain

<400> SEQUENCE: 1

Trp Val Leu Thr Ala Ala His Cys Lys Lys Pro Asn Leu Gln Val
                5                   10                  15

Phe Leu Glu Lys His Asn Leu Arg Gln Arg Glu Ser Ser Gln Glu
                20                  25                  30

Gln Ser Ser Val Val Arg Ala Val Ile His Pro Asp Tyr Asp Ala
                35                  40                  45

Ala Ser His Asp Gln Asp Ile Met Leu Leu Arg Leu Ala Arg Pro
                50                  55                  60

Ala Lys Leu Ser Glu Leu Ile Gln Pro Leu Pro Leu Glu Arg Asp
                65                  70                  75

Cys Ser Ala Asn Thr Thr Ser Cys His Ile Leu Gly Trp Gly Lys
                80                  85                  90

Thr Ala Asp Gly Asp Phe Pro Asp Thr Ile Gln Cys Ala Tyr Ile
                95                  100                 105

His Leu Val Ser Arg Glu Glu Cys Glu His Ala Tyr Pro Gly Gln
                110                 115                 120

```
Ile Thr Gln Asn Met Leu Cys Ala Gln Asp Glu Lys Tyr Gly Lys
            125                 130                 135

Asp Ser Cys Gln Gly Asp Ser Gly Gly
            140

<210> SEQ ID NO 2
<211> LENGTH: 148
<212> TYPE: PRT
<213> ORGANISM: Homo sapiens
<220> FEATURE:
<222> LOCATION: DOMAIN
<223> OTHER INFORMATION: Amino acid sequence of TADG-14 catalytic domain

<400> SEQUENCE: 2

Trp Val Val Thr Ala Ala His Cys Lys Lys Pro Lys Tyr Thr Val
              5                  10                  15

Arg Leu Gly Asp His Ser Leu Gln Asn Lys Asp Gly Pro Glu Gln
             20                  25                  30

Glu Ile Pro Val Val Gln Ser Ile Pro His Pro Cys Tyr Asn Ser
             35                  40                  45

Ser Asp Val Glu Asp His Asn His Asp Leu Met Leu Leu Gln Leu
             50                  55                  60

Arg Asp Gln Ala Ser Leu Gly Ser Lys Val Lys Pro Ile Ser Leu
             65                  70                  75

Ala Asp His Cys Thr Gln Pro Gly Gln Asn Cys Thr Val Ser Gly
             80                  85                  90

Trp Gly Thr Val Thr Ser Pro Arg Glu Asn Phe Pro Asp Thr Leu
             95                 100                 105

Asn Cys Ala Glu Val Lys Ile Phe Pro Gln Lys Lys Cys Glu Asp
            110                 115                 120

Ala Tyr Pro Gly Gln Ile Thr Asp Gly Met Val Cys Ala Gly Ser
            125                 130                 135

Ser Lys Gly Ala Asp Thr Cys Gln Gly Asp Ser Gly Gly
            140                 145

<210> SEQ ID NO 3
<211> LENGTH: 146
<212> TYPE: PRT
<213> ORGANISM: unknown
<220> FEATURE:
<221> NAME/KEY: DOMAIN
<223> OTHER INFORMATION: Amino acid sequence of trypsin like serine
      protease (Try1) catalytic domain

<400> SEQUENCE: 3

Trp Val Val Ser Ala Gly His Cys Tyr Lys Ser Arg Ile Gln Val
              5                  10                  15

Arg Leu Gly Glu His Asn Ile Glu Val Leu Glu Gly Asn Glu Gln
             20                  25                  30

Phe Ile Asn Ala Ala Lys Ile Ile Arg His Pro Gln Tyr Asp Arg
             35                  40                  45

Lys Thr Leu Asn Asn Asp Ile Met Leu Ile Lys Leu Ser Ser Arg
             50                  55                  60

Ala Val Ile Asn Ala Arg Val Ser Thr Ile Ser Leu Pro Thr Ala
             65                  70                  75

Pro Pro Ala Thr Gly Thr Lys Cys Leu Ile Ser Gly Trp Gly Asn
             80                  85                  90

Thr Ala Ser Ser Gly Ala Asp Tyr Pro Asp Glu Leu Gln Cys Leu
```

```
                     95                 100                 105
Asp Ala Pro Val Leu Ser Gln Ala Lys Cys Glu Ala Ser Tyr Pro
            110                 115                 120
Gly Lys Ile Thr Ser Asn Met Phe Cys Val Gly Phe Leu Glu Gly
            125                 130                 135
Gly Lys Asp Ser Cys Gln Gly Asp Ser Gly Gly
            140                 145
```

<210> SEQ ID NO 4
<211> LENGTH: 144
<212> TYPE: PRT
<213> ORGANISM: unknown
<220> FEATURE:
<221> NAME/KEY: DOMAIN
<223> OTHER INFORMATION: Amino acid sequence of stratum corneum
      chymotryptic enzyme (scce) catalytic domain

<400> SEQUENCE: 4

```
Trp Val Leu Thr Ala Ala His Cys Lys Met Asn Glu Tyr Thr Val
                  5                  10                  15
His Leu Gly Ser Asp Thr Leu Gly Asp Arg Arg Ala Gln Arg Ile
             20                  25                  30
Lys Ala Ser Lys Ser Phe Arg His Pro Gly Tyr Ser Thr Gln Thr
             35                  40                  45
His Val Asn Asp Leu Met Leu Val Lys Leu Asn Ser Gln Ala Arg
             50                  55                  60
Leu Ser Ser Met Val Lys Lys Val Arg Leu Pro Ser Arg Cys Glu
             65                  70                  75
Pro Pro Gly Thr Thr Cys Thr Val Ser Gly Trp Gly Thr Thr Thr
             80                  85                  90
Ser Pro Asp Val Thr Phe Pro Ser Asp Leu Met Cys Val Asp Val
             95                 100                 105
Lys Leu Ile Ser Pro Gln Asp Cys Thr Lys Val Tyr Lys Asp Leu
            110                 115                 120
Leu Glu Asn Ser Met Leu Cys Ala Gly Ile Pro Asp Ser Lys Lys
            125                 130                 135
Asn Ala Cys Asn Gly Asp Ser Gly Gly
            140
```

<210> SEQ ID NO 5
<211> LENGTH: 159
<212> TYPE: PRT
<213> ORGANISM: unknown
<220> FEATURE:
<221> NAME/KEY: DOMAIN
<223> OTHER INFORMATION: Amino acid sequence of hepsin (heps) catalytic
      domain

<400> SEQUENCE: 5

```
Trp Val Leu Thr Ala Ala His Cys Phe Pro Glu Arg Asn Arg Val
                  5                  10                  15
Leu Ser Arg Trp Arg Val Phe Ala Gly Ala Val Ala Gln Ala Ser
             20                  25                  30
Pro His Gly Leu Gln Leu Gly Val Gln Ala Val Val Tyr His Gly
             35                  40                  45
Gly Tyr Leu Pro Phe Arg Asp Pro Asn Ser Glu Glu Asn Ser Asn
             50                  55                  60
Asp Ile Ala Leu Val His Leu Ser Ser Pro Leu Pro Leu Thr Glu
             65                  70                  75
```

```
Tyr Ile Gln Pro Val Cys Leu Pro Ala Ala Gly Gln Ala Leu Val
                80                  85                  90

Asp Gly Lys Ile Cys Thr Val Thr Gly Trp Gly Asn Thr Gln Tyr
            95                  100                 105

Tyr Gly Gln Gln Ala Gly Val Leu Gln Glu Ala Arg Val Pro Ile
        110                 115                 120

Ile Ser Asn Asp Val Cys Asn Gly Ala Asp Phe Tyr Gly Asn Gln
    125                 130                 135

Ile Lys Pro Lys Met Phe Cys Ala Gly Tyr Pro Glu Gly Gly Ile
140                 145                 150

Asp Ala Cys Gln Gly Asp Ser Gly Gly
                155
```

```
<210> SEQ ID NO 6
<211> LENGTH: 1343
<212> TYPE: DNA
<213> ORGANISM: Homo sapiens
<220> FEATURE:
<223> OTHER INFORMATION: Nucleotide sequence encoding Tumor Antigen
      Derived Gene-14 (TADG-14) protein;

<400> SEQUENCE: 6
ctgtagcagg cagagcttac caagtctctc cgaactcaaa tggaagaaat accttatgaa      60
tgtaagaatg taggggggtca tggcttgtaa tttacacagt gtaaatgaaa ccatcctaga    120
ggattatgag gaatcctttc tatgtgattt tcaatcatag caagcaagaa aggctccagt     180
gtcaaggtag ttcagctctt acaggatata aaacagtcca tacttgagag aaaaaactta     240
gatctgagtg atggaatgtg aagcaaatct ttcaaaatca gtagacattt cttggacata    300
aaacacagat gaggaaaggg cttcaaatta gaagttacgt aatcaccatc agaaagttca     360
tgtttggtaa attctgttac tagaaatgta ggaaattcag gtatagcttt gaatcccaat    420
tacacattgg tcagtgggaa aactaagggc ctccaacagg caaattcagg gaggataggt    480
ttcagggaat gccctggatt ctggaagacc tcaccatggg acgcccccga cctcgtgcgg    540
ccaagacgtg gatgttcctg ctcttgctgg ggggagcctg gcaggacac tccagggcac     600 aggaggacaa ggtgctgggg ggtcatgagt gccaacccca ttcgcagcct tggcaggcgg    660
ccttgttcca gggccagcaa ctactctgtg gcggtgtcct tgtaggtggc aactgggtcc    720
ttacagctgc ccactgtaaa aaccgaaat acacagtacg cctgggagac cacagcctac     780
agaataaaga tggcccagag caagaaatac ctgtggttca gtccatccca cacccctgct    840
acaacagcag cgatgtggag gaccacaacc atgatctgat gcttcttcaa ctgcgtgacc    900
aggcatccct ggggtccaaa gtgaagccca tcagcctggc agatcattgc acccagcctg    960
gccagaagtg caccgtctca ggctggggca ctgtcaccag tccccgagag aattttcctg   1020
acactctcaa ctgtgcagaa gtaaaaatct ttccccagaa gaagtgtgag gatgcttacc   1080
cggggcagat cacagatggc atggtctgtg caggcagcag caaggggct gacacgtgcc    1140 agggcgattc tggaggcccc ctggtgtgtg atggtgcact ccaggggcat acatcctggg   1200
gctcagaccc ctgtgggagg tccgacaaac ctggcgtcta taccaacatc tgccgctacc   1260
tggactggat caagaagatc ataggcagca agggctgatt ctaggataag cactagatct   1320
cccttaataa actcacggaa ttc                                            1343
```

```
<210> SEQ ID NO 7
<211> LENGTH: 260
```

<212> TYPE: PRT
<213> ORGANISM: Homo sapiens
<220> FEATURE:
<223> OTHER INFORMATION: Amino acid sequence of TADG-14 protein

<400> SEQUENCE: 7

```
Met Gly Arg Pro Arg Pro Arg Ala Ala Lys Thr Trp Met Phe Leu
                 5                  10                  15
Leu Leu Leu Gly Gly Ala Trp Ala Gly His Ser Arg Ala Gln Glu
             20                  25                  30
Asp Lys Val Leu Gly Gly His Glu Cys Gln Pro His Ser Gln Pro
             35                  40                  45
Trp Gln Ala Ala Leu Phe Gln Gly Gln Gln Leu Leu Cys Gly Gly
             50                  55                  60
Val Leu Val Gly Gly Asn Trp Val Leu Thr Ala Ala His Cys Lys
             65                  70                  75
Lys Pro Lys Tyr Thr Val Arg Leu Gly Asp His Ser Leu Gln Asn
             80                  85                  90
Lys Asp Gly Pro Glu Gln Glu Ile Pro Val Val Gln Ser Ile Pro
             95                 100                 105
His Pro Cys Tyr Asn Ser Ser Asp Val Glu Asp His Asn His Asp
            110                 115                 120
Leu Met Leu Leu Gln Leu Arg Asp Gln Ala Ser Leu Gly Ser Lys
            125                 130                 135
Val Lys Pro Ile Ser Leu Ala Asp His Cys Thr Gln Pro Gly Gln
            140                 145                 150
Lys Cys Thr Val Ser Gly Trp Gly Thr Val Thr Ser Pro Arg Glu
            155                 160                 165
Asn Phe Pro Asp Thr Leu Asn Cys Ala Glu Val Lys Ile Phe Pro
            170                 175                 180
Gln Lys Lys Cys Glu Asp Ala Tyr Pro Gly Gln Ile Thr Asp Gly
            185                 190                 195
Met Val Cys Ala Gly Ser Ser Lys Gly Ala Asp Thr Cys Gln Gly
            200                 205                 210
Asp Ser Gly Gly Pro Leu Val Cys Asp Gly Ala Leu Gln Gly Ile
            215                 220                 225
Thr Ser Trp Gly Ser Asp Pro Cys Gly Arg Ser Asp Lys Pro Gly
            230                 235                 240
Val Tyr Thr Asn Ile Cys Arg Tyr Leu Asp Trp Ile Lys Lys Ile
            245                 250                 255
Ile Gly Ser Lys Gly
            260
```

<210> SEQ ID NO 8
<211> LENGTH: 799
<212> TYPE: DNA
<213> ORGANISM: Mus sp.
<220> FEATURE:
<222> LOCATION: 477..1275
<223> OTHER INFORMATION: Nucleotide sequence of mouse neuropsin homologous to TADG-14

<400> SEQUENCE: 8

```
agaggccacc atgggacgcc cccaccctg tgcaatccag ccgtggatcc ttctgcttct    60
gttcatggga gcgtgggcag ggctcaccag agctcagggc tccaagatcc tggaaggtcg   120
agagtgtata ccccactccc agccttggca ggcagccttg ttccagggcg agagactgat   180
```

```
ctgtggggt gtcctggttg agacagatg ggtcctcacg gcagcccact gcaaaaaaca      240
gaagtactcc gtgcgtctgg gtgatcatag cctccagagc agagatcagc cggagcagga    300
gatccaggtg gctcagtcta tccagcatcc ttgctacaac aacagcaacc cagaagatca   360
cagtcacgat ataatgctca ttcgactgca gaactcagca aacctcgggg acaaggtgaa    420
gccggtccaa ctggccaatc tgtgtcccaa agttggccag aagtgcatca tatcaggctg    480
gggcactgtc accagccctc aagagaactt tccaaacacc ctcaactgtg cggaagtgaa    540
aatctattcc cagaacaagt gtgagagagc ctatccaggg aagatcaccg agggcatggt    600
ctgtgctggc agcagcaatg agctgacacg tgccagggt gactcaggag ccctctggt     660 gtgcgacggg atgctccagg gcatcacctc atggggctca gacccctgtg ggaaacccga    720
gaaacctgga gtctacacca aaatctgccg ctacactacc tggatcaaga agaccatgga    780
caacagggac tgatcctgg                                                 799
```

<210> SEQ ID NO 9
<211> LENGTH: 799
<212> TYPE: DNA
<213> ORGANISM: Homo sapiens
<220> FEATURE:
<222> LOCATION: 506...1304
<223> OTHER INFORMATION: Nucleotide sequence of TADG-14 homologous to mouse neuropsin

<400> SEQUENCE: 9

```
agacctcacc atgggacgcc cccgacctcg tgcggccaag acgtggatgt tcctgctctt    60
gctgggggga gcctgggcag acactccag ggcacaggag gacaaggtgc tggggggtca    120
tgagtgccaa ccccattcgc agccttggca ggcggccttg ttccagggcc agcaactact   180
ctgtggcggt gtccttgtag gtggcaactg ggtccttaca gctgcccact gtaaaaaacc    240
gaaatacaca gtacgcctgg gagaccacag cctacagaat aaagatggcc agagcaaga    300 aatacctgtg gttcagtcca tcccacaccc ctgctacaac agcagcgatg tggaggacca    360
caaccatgat ctgatgcttc ttcaactgcg tgaccaggca tccctggggt ccaaagtgaa    420
gcccatcagc ctggcagatc attgcaccca gcctggccag aagtgcaccg tctcaggctg    480
gggcactgtc accagtcccc gagagaattt tcctgacact ctcaactgtg cagaagtaaa    540
aatctttccc cagaagaagt gtgaggatgc ttacccgggg cagatcacag atggcatggt    600
ctgtgcaggc agcagcaaag gggctgacac gtgccaggc gattctggag ccccctggt    660 gtgtgatggt gcactccagg gcatcacatc ctggggctca gacccctgtg ggaggtccga    720
caaacctggc gtctatacca acatctgccg ctacctggac tggatcaaga agatcatagg    780
cagcaagggc tgattctag                                                 799
```

<210> SEQ ID NO 10
<211> LENGTH: 260
<212> TYPE: PRT
<213> ORGANISM: Mus sp.
<220> FEATURE:
<223> OTHER INFORMATION: Amino acid sequence of mouse neuropsin homologous to TADG-14; accession no. D30785

<400> SEQUENCE: 10

Met Gly Arg Pro Pro Pro Cys Ala Ile Gln Pro Trp Ile Leu Leu
                5                   10                  15

Leu Leu Phe Met Gly Ala Trp Ala Gly Leu Thr Arg Ala Gln Gly
                20                  25                  30

```
Ser Lys Ile Leu Glu Gly Arg Glu Cys Ile Pro His Ser Gln Pro
            35                  40                  45

Trp Gln Ala Ala Leu Phe Gln Gly Glu Arg Leu Ile Cys Gly Gly
            50                  55                  60

Val Leu Val Gly Asp Arg Trp Val Leu Thr Ala Ala His Cys Lys
            65                  70                  75

Lys Gln Lys Tyr Ser Val Arg Leu Gly Asp His Ser Leu Gln Ser
            80                  85                  90

Arg Asp Gln Pro Glu Gln Glu Ile Gln Val Ala Gln Ser Ile Gln
            95                 100                 105

His Pro Cys Tyr Asn Asn Ser Asn Pro Glu Asp His Ser His Asp
           110                 115                 120

Ile Met Leu Ile Arg Leu Gln Asn Ser Ala Asn Leu Gly Asp Lys
           125                 130                 135

Val Lys Pro Val Gln Leu Ala Asn Leu Cys Pro Lys Val Gly Gln
           140                 145                 150

Lys Cys Ile Ile Ser Gly Trp Gly Thr Val Thr Ser Pro Gln Glu
           155                 160                 165

Asn Phe Pro Asn Thr Leu Asn Cys Ala Glu Val Lys Ile Tyr Ser
           170                 175                 180

Gln Asn Lys Cys Glu Arg Ala Tyr Pro Gly Lys Ile Thr Glu Gly
           185                 190                 195

Met Val Cys Ala Gly Ser Ser Asn Gly Ala Asp Thr Cys Gln Gly
           200                 205                 210

Asp Ser Gly Gly Pro Leu Val Cys Asp Gly Met Leu Gln Gly Ile
           215                 220                 225

Thr Ser Trp Gly Ser Asp Pro Cys Gly Lys Pro Glu Lys Pro Gly
           230                 235                 240

Val Tyr Thr Lys Ile Cys Arg Tyr Thr Thr Trp Ile Lys Lys Thr
           245                 250                 255

Met Asp Asn Arg Asp
           260

<210> SEQ ID NO 11
<211> LENGTH: 262
<212> TYPE: PRT
<213> ORGANISM: Homo sapiens
<220> FEATURE:
<223> OTHER INFORMATION: Amino acid sequence of human glandular
      kallikrein (hHk2); accession no. P06870

<400> SEQUENCE: 11

Met Trp Phe Val Leu Cys Leu Ala Leu Ser Leu Gly Gly Thr Gly
             5                  10                  15

Ala Ala Pro Pro Ile Gln Ser Arg Ile Val Gly Gly Trp Glu
            20                  25                  30

Gly Glu Gln His Ser Gln Pro Trp Gln Ala Ala Leu Tyr His Phe
            35                  40                  45

Ser Thr Phe Gln Cys Gly Gly Ile Leu Val His Arg Gln Trp Val
            50                  55                  60

Leu Thr Ala Ala His Cys Ile Ser Asp Asn Tyr Gln Leu Trp Leu
            65                  70                  75

Gly Arg His Asn Leu Phe Asp Asp Glu Asn Thr Ala Gln Phe Val
            80                  85                  90

His Val Ser Glu Ser Phe Pro His Pro Gly Phe Asn Met Ser Leu
            95                 100                 105
```

```
Leu Glu Asn His Thr Arg Gln Ala Asp Glu Asp Tyr Ser His Asp
            110                 115                 120

Leu Met Leu Leu Arg Leu Thr Glu Pro Ala Asp Thr Ile Thr Asp
            125                 130                 135

Ala Val Lys Val Val Glu Leu Pro Thr Gln Glu Pro Glu Val Gly
            140                 145                 150

Ser Thr Cys Leu Ala Ser Gly Trp Gly Ser Ile Glu Pro Glu Asn
            155                 160                 165

Phe Ser Phe Pro Asp Asp Leu Gln Cys Val Asp Leu Lys Ile Leu
            170                 175                 180

Pro Asn Asp Glu Cys Glu Lys Ala His Val Gln Lys Val Thr Asp
            185                 190                 195

Phe Met Leu Cys Val Gly His Leu Glu Gly Gly Lys Asp Thr Cys
            200                 205                 210

Val Gly Asp Ser Gly Gly Pro Leu Met Cys Asp Gly Val Leu Gln
            215                 220                 225

Gly Val Thr Ser Trp Gly Tyr Val Pro Cys Gly Thr Pro Asn Lys
            230                 235                 240

Pro Ser Val Ala Val Arg Val Leu Ser Tyr Val Lys Trp Ile Glu
            245                 250                 255

Asp Thr Ile Ala Glu Asn Ser
            260

<210> SEQ ID NO 12
<211> LENGTH: 261
<212> TYPE: PRT
<213> ORGANISM: Homo sapiens
<220> FEATURE:
<223> OTHER INFORMATION: Amino acid sequence of Prostate Specific
      Antigen (hPSA); accession no. P07288

<400> SEQUENCE: 12

Met Trp Val Pro Val Val Phe Leu Thr Leu Ser Val Thr Trp Ile
              5                  10                  15

Gly Ala Ala Pro Leu Ile Leu Ser Arg Ile Val Gly Gly Trp Glu
             20                  25                  30

Cys Glu Lys His Ser Gln Pro Trp Gln Val Leu Val Ala Ser Arg
             35                  40                  45

Gly Arg Ala Val Cys Gly Gly Val Leu Val His Pro Gln Trp Val
             50                  55                  60

Leu Thr Ala Ala His Cys Ile Arg Asn Lys Ser Val Ile Leu Leu
             65                  70                  75

Gly Arg His Ser Leu Phe His Pro Glu Asp Thr Gly Gln Val Phe
             80                  85                  90

Gln Val Ser His Ser Phe Pro His Pro Leu Tyr Asp Met Ser Leu
             95                 100                 105

Leu Lys Asn Arg Phe Leu Arg Pro Gly Asp Asp Ser Ser His Asp
            110                 115                 120

Leu Met Leu Leu Arg Leu Ser Glu Pro Ala Glu Leu Thr Asp Ala
            125                 130                 135

Val Lys Val Met Asp Leu Pro Thr Gln Glu Pro Ala Leu Gly Thr
            140                 145                 150

Thr Cys Tyr Ala Ser Gly Trp Gly Ser Ile Glu Pro Glu Glu Phe
            155                 160                 165

Leu Thr Pro Lys Lys Leu Gln Cys Val Asp Leu His Val Ile Ser
            170                 175                 180
```

```
Asn Asp Val Cys Ala Gln Val His Pro Gln Lys Val Thr Lys Phe
            185                 190                 195

Met Leu Cys Ala Gly Arg Trp Thr Gly Gly Lys Ser Thr Cys Ser
            200                 205                 210

Gly Asp Ser Gly Gly Pro Leu Val Cys Asn Gly Val Leu Gln Gly
            215                 220                 225

Ile Thr Ser Trp Gly Ser Glu Pro Cys Ala Leu Pro Glu Arg Pro
            230                 235                 240

Ser Leu Tyr Thr Lys Val Val His Tyr Arg Lys Trp Ile Lys Asp
            245                 250                 255

Thr Ile Val Ala Asn Pro
            260

<210> SEQ ID NO 13
<211> LENGTH: 244
<212> TYPE: PRT
<213> ORGANISM: Homo sapiens
<220> FEATURE:
<223> OTHER INFORMATION: Amino acid sequence of human protease m
      (hProM); accession No. U62801

<400> SEQUENCE: 13

Met Lys Lys Leu Met Val Val Leu Ser Leu Ile Ala Ala Ala Trp
              5                  10                  15

Ala Glu Glu Gln Asn Lys Leu Val His Gly Gly Pro Cys Asp Lys
             20                  25                  30

Thr Ser His Pro Tyr Gln Ala Ala Leu Thr Tyr Ser Gly His Leu
             35                  40                  45

Leu Cys Gly Gly Val Leu Ile His Pro Leu Trp Val Leu Thr Ala
             50                  55                  60

Ala His Cys Lys Lys Pro Asn Leu Gln Val Phe Leu Gly Lys His
             65                  70                  75

Asn Leu Arg Gly Arg Glu Ser Ser Gln Glu Gln Ser Ser Val Val
             80                  85                  90

Arg Ala Val Ile His Pro Asp Tyr Asp Ala Ala Ser His Asp Gln
             95                 100                 105

Asp Ile Met Leu Leu Arg Leu Ala Arg Pro Ala Lys Leu Ser Glu
            110                 115                 120

Leu Ile Gln Pro Leu Pro Leu Glu Arg Asp Cys Ser Ala Asn Thr
            125                 130                 135

Thr Ser Cys His Ile Leu Gly Trp Gly Lys Thr Ala Asp Gly Asp
            140                 145                 150

Phe Pro Asp Thr Ile Gln Cys Ala Tyr Ile His Leu Val Ser Arg
            155                 160                 165

Glu Glu Cys Glu His Ala Tyr Pro Gly Gln Ile Thr Gln Asn Met
            170                 175                 180

Leu Cys Ala Gly Asp Glu Lys Tyr Gly Lys Asp Ser Cys Gln Gly
            185                 190                 195

Asp Ser Gly Gly Pro Leu Val Cys Gly Asp His Ile Arg Gly Leu
            200                 205                 210

Val Ser Trp Gly Asn Ile Pro Cys Gly Ser Lys Glu Lys Pro Gly
            215                 220                 225

Val Tyr Thr Asn Val Cys Arg Tyr Thr Asn Trp Ile Gln Lys Thr
            230                 235                 240

Ile Gln Ala Lys
```

```
<210> SEQ ID NO 14
<211> LENGTH: 20
<212> TYPE: DNA
<213> ORGANISM: artificial sequence
<220> FEATURE:
<221> NAME/KEY: primer
<223> OTHER INFORMATION: Sense primer for TADG-14 specific PCR

<400> SEQUENCE: 14
acagtacgcc tgggagacca                                               20

<210> SEQ ID NO 15
<211> LENGTH: 20
<212> TYPE: DNA
<213> ORGANISM: artificial sequence
<220> FEATURE:
<221> NAME/KEY: primer
<223> OTHER INFORMATION: Anti-sense primer for TADG-14 specific PCR

<400> SEQUENCE: 15
ctgagacggt gcaattctgg                                               20

<210> SEQ ID NO 16
<211> LENGTH: 12
<212> TYPE: PRT
<213> ORGANISM: artificial sequence
<220> FEATURE:
<223> OTHER INFORMATION: Peptide sequence of immunogenic poly-lysine
      linked multiple antigen (T14-1) derived from
      TADG-14 used to produce polyclonal antibodies

<400> SEQUENCE: 16

Lys Tyr Thr Val Arg Leu Gly Asp His Ser Leu Gln
                 5                  10

<210> SEQ ID NO 17
<211> LENGTH: 12
<212> TYPE: PRT
<213> ORGANISM: artificial sequence
<220> FEATURE:
<223> OTHER INFORMATION: Peptide sequence of immunogenic poly-lysine
      linked multiple antigen (T14-2) derived from
      TADG-14 used to produce polyclonal antibodies

<400> SEQUENCE: 17

Gly His Glu Cys Gln Pro His Ser Gln Pro Trp Gln
                 5                  10

<210> SEQ ID NO 18
<211> LENGTH: 12
<212> TYPE: PRT
<213> ORGANISM: artificial sequence
<220> FEATURE:
<223> OTHER INFORMATION: Peptide sequence of immunogenic poly-lysine
      linked multiple antigen (T14-3) derived from
      TADG-14 used to produce polyclonal antibodies

<400> SEQUENCE: 18

Leu Asp Trp Ile Lys Lys Ile Ile Gly Ser Lys Gly
1                5                  10
```